US010976317B2

(12) United States Patent
Patel et al.

(10) Patent No.: US 10,976,317 B2
(45) Date of Patent: *Apr. 13, 2021

(54) SYSTEMATIC DISCOVERY, MATURATION AND EXTENSION OF PEPTIDE BINDERS TO PROTEINS

(71) Applicant: Roche Sequencing Solutions, Inc., Pleasanton, CA (US)

(72) Inventors: Jigar Patel, Madison, WI (US); Victor Lyamichev, Madison, WI (US); Thomas Albert, Danville, CA (US)

(73) Assignee: Roche Sequencing Solutions, Inc., Pleasanton, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/191,407

(22) Filed: Nov. 14, 2018

(65) Prior Publication Data

US 2019/0086411 A1    Mar. 21, 2019

Related U.S. Application Data

(63) Continuation of application No. 14/577,334, filed on Dec. 19, 2014, now Pat. No. 10,161,938.

(60) Provisional application No. 61/921,259, filed on Dec. 27, 2013, provisional application No. 61/921,263, filed on Dec. 27, 2013.

(51) Int. Cl.
| | |
|---|---|
| *C40B 30/04* | (2006.01) |
| *G01N 33/573* | (2006.01) |
| *C07K 1/04* | (2006.01) |
| *G01N 33/574* | (2006.01) |
| *G01N 33/68* | (2006.01) |
| *C07K 7/06* | (2006.01) |

(52) U.S. Cl.
CPC .......... *G01N 33/573* (2013.01); *C07K 1/047* (2013.01); *C07K 7/06* (2013.01); *G01N 33/57434* (2013.01); *G01N 33/6845* (2013.01); *C40B 30/04* (2013.01); *G01N 2333/36* (2013.01)

(58) Field of Classification Search
None
See application file for complete search history.

(56) References Cited

U.S. PATENT DOCUMENTS

2010/0160071 A1    6/2010  Burrows

FOREIGN PATENT DOCUMENTS

| | | |
|---|---|---|
| EP | 1 914 550 A1 | 4/2008 |
| JP | 2007-259856 A | 10/2007 |
| WO | WO-93/18054 A2 | 9/1993 |
| WO | WO-96/03649 A1 | 2/1996 |
| WO | WO-97/22617 A1 | 6/1997 |
| WO | WO-02/31510 A1 | 4/2002 |

(Continued)

OTHER PUBLICATIONS

Rickles et al. (Dec. 1, 1994) EMBO Journal vol. 13 pp. 5598 to 5604.*

(Continued)

*Primary Examiner* — Christian C Boesen
(74) *Attorney, Agent, or Firm* — Foley & Lardner LLP

(57) ABSTRACT

The invention comprises systems, methods and arrays for identification and optimization of novel peptide binders to protein targets. Embodiments include steps of peptide binder discovery, core peptide maturation, N-terminal and C-terminal extension and kinetics analysis of the final peptide binder.

16 Claims, 12 Drawing Sheets

Specification includes a Sequence Listing.

(56) References Cited

FOREIGN PATENT DOCUMENTS

| WO | WO-03/029288 A2 | 4/2003 |
| WO | WO-2004/001064 A2 | 12/2003 |
| WO | WO-2005/025497 A2 | 3/2005 |
| WO | WO-2005/088310 A2 | 9/2005 |
| WO | WO-2010/052939 A1 | 5/2010 |
| WO | WO-2013/119845 A1 | 8/2013 |

OTHER PUBLICATIONS

Administrator: "Peptide Libraries", Apr. 21, 2009, XP0551774, 8 pages.

Bolger, et al., Scanning Peptide Array Analyses Identify Overlapping Binding Sites for the Signalling Scaffold Proteins, beta-Arrestin and RACK1, in cAMP-specific Phosphodiesterase PDED5, Biochemical Journal, Aug. 15, 2006, vol. 398, Pt. 1, pp. 23-36.

Choe, et al., "Substrate Profiling of Cysteine Proteases Using a Combinatonal Peptide Library Identifies Functionally Unique Specificities", May 5, 2006, J. of Biological Chemistry, vol. 281, No. 18, pp. 12824-12832.

Communication pursuant to Article 94(3) EPC in EP Patent Application No. 14821163.4 dated May 5, 2018 (5 pages).

Hanes, et al., "Picomolar Affinity Antibodies from a Fully Synthetic Na?ve Library Selected and Evolved by Ribosome Display", Dec. 2000, Nature Biotechnology, vol. 18, pp. 1287-1292.

Hilpert, et al., "Anti-C-Myc Antibody 9E10: Epitope Key Positions and Variability Characterized using Peptide Spot Synthesis on Cellulose", Protein Engineering, Oct. 1, 2001, vol. 14, Issue 10, pp. 803-806.

International Search Report and Written Opinion in International Patent Application No. PCT/EP2014/078658 dated Jun. 29, 2015 (14 pages).

Katz, et al., "Studying Protein-protein Interactions Using Peptide Arrays", May 2011, Chem. Soc. Rev. vol. 40, pp. 2131-2145.

Lowman, et al., "Bacteriophage Display and Discovery of Peptide Leads for Drug Development", Annual Review of Biophysics and Biomolecular Structure, Jan. 1, 1997, vol. 26, pp. 401-424.

Non-Final Office Action in U.S. Appl. No. 14/577,334 dated Dec. 28, 2017 (11 pages).

Non-Final Office Action in U.S. Appl. No. 14/577,334 dated Jun. 29, 2017 (11 pages).

Notice of Reasons for Refusal in JP Patent Application No. 2016-541379 dated May 11, 2017 (with English translation) (9 pages).

Raffler, et al., A Novel Class of Small Functional Peptides that Bind and Inhibit Human Thrombin Isolated by mRNA Display, Jan. 2003, Chemistry and Biology, vol. 10, Issue 1, pp. 69-79.

Rickles, et al., "Phage display selection of ligand residues important for Src homology 3 domain binding specificity", Nov. 21, 1995, Proceedings of the National Academy of Sciences, vol. 6, No. 1, pp. 109-122.

Schmidt, et al., "The Random Peptide Library-Assisted Engineering of a C-Terminal Affinity Peptide, Useful for the Detection and Purification of a Functional IG FV Fragment", Jan. 1, 1993, Protein Engineering, vol. 6, No. 1, pp. 109-122.

Shin, et al., "Combinatorial Solid Phase Peptide Synthesis and Bioassays", Sep. 1, 2005, Journal of Biochem. and Mol. Bio., vol. 38, No. 5, pp. 517-525.

White, et al., "Standardizing and Simplifying Analysis of Peptide Library Data", Journal of Chemical Information and Modeling, Jan. 17, 2013, vol. 53, Issue 2, pp. 493-499.

Wilson, et al., "The Use of mRNA Display to Select High-Affinity Protein-Binding Peptides", PNAS, Mar. 27, 2001, vol. 98, No. 7, pp. 3750-3755.

Yu, et al., "Structural Basis for the Binding of Proline-rich Peptides to DH3 Domains", Cell, Mar. 11, 1994, vol. 76, No. 5, pp. 933-945.

* cited by examiner

SEQUENCE LISTING

<160> NUMBER OF SEQ ID NOS: 85

<210> SEQ ID NO 1
<211> LENGTH: 5
<212> TYPE: PRT
<213> ORGANISM: Artificial Sequence
<220> FEATURE:
<223> OTHER INFORMATION: Description of Artificial Sequence: Synthetic peptide

<400> SEQUENCE: 1

Phe Glu Val Tyr Leu
1               5

<210> SEQ ID NO 2
<211> LENGTH: 5
<212> TYPE: PRT
<213> ORGANISM: Artificial Sequence
<220> FEATURE:

```
<223> OTHER INFORMATION: Description of Artificial Sequence: Synthetic
      peptide

<400> SEQUENCE: 2

Trp Thr Val Tyr Ala
1               5

<210> SEQ ID NO 3
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Trp Glu Val His Leu
1               5

<210> SEQ ID NO 4
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Arg Ser Ile Leu Tyr
1               5

<210> SEQ ID NO 5
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Asn Gly Phe Glu Val Tyr Leu Pro Gly
1               5

<210> SEQ ID NO 6
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Ser Glu Trp Thr Val Tyr Ala Gly Asn
1               5

<210> SEQ ID NO 7
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Thr Gly Trp Glu Val His Leu Gly Lys
1               5
```

```
<210> SEQ ID NO 8
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Ser Cys Arg Ser Ile Leu Tyr Gly Gln
1               5

<210> SEQ ID NO 9
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Gly Thr Gly Phe Glu Val Tyr Ile Pro Gly Ala
1               5                   10

<210> SEQ ID NO 10
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Ala Ser Glu Trp Thr Val Tyr Ala Gly Asn Lys
1               5                   10

<210> SEQ ID NO 11
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Gly Thr Gly Trp Glu Val His Leu Gly Lys Gly
1               5                   10

<210> SEQ ID NO 12
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Gln Ser Cys Arg Ser Ile Leu Tyr Gly Asp Gly
1               5                   10

<210> SEQ ID NO 13
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13
```

His Pro Gln
1

<210> SEQ ID NO 14
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Leu Ala Glu Tyr His
1               5

<210> SEQ ID NO 15
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Arg Pro Gly Trp Lys
1               5

<210> SEQ ID NO 16
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Pro Ala Trp Ala His
1               5

<210> SEQ ID NO 17
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Phe Asp Glu Trp Leu
1               5

<210> SEQ ID NO 18
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Trp Thr His Pro Gln Phe Glu
1               5

<210> SEQ ID NO 19
<211> LENGTH: 9
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 19

Asp Tyr Leu Ala Glu Tyr His Gly Gly
1               5

<210> SEQ ID NO 20
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Tyr Glu Arg Pro Gly Trp Lys Leu Ser
1               5

<210> SEQ ID NO 21
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Pro Ala Pro Ala Trp Ala His Gly Gly
1               5

<210> SEQ ID NO 22
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Asn Ser Phe Asp Glu Trp Leu Gln Lys
1               5

<210> SEQ ID NO 23
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Trp Thr His Pro Gln Phe Glu Gln Lys
1               5

<210> SEQ ID NO 24
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Ala Asp Tyr Leu Ala Glu Tyr His Gly Gly
1               5                   10
```

```
<210> SEQ ID NO 25
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Tyr Glu Arg Pro Gly Trp Lys Leu Gly Thr
1               5                   10

<210> SEQ ID NO 26
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Asp Pro Ala Pro Ala Trp Ala His Gly Gly
1               5                   10

<210> SEQ ID NO 27
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Asn Ser Phe Asp Asp Trp Leu Ala Lys Gly Gly
1               5                   10

<210> SEQ ID NO 28
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Gly Ala Val Asp Pro Ser Glu Leu Thr
1               5

<210> SEQ ID NO 29
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Leu Ala Asp Lys Thr Gln Pro Phe Val Tyr
1               5                   10

<210> SEQ ID NO 30
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 30

His Pro Gln Ala
1

<210> SEQ ID NO 31
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Tyr His Pro Gln
1

<210> SEQ ID NO 32
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

Gly Gly Trp Thr His Pro Gln Phe Glu Gly Gly
1               5                   10

<210> SEQ ID NO 33
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

Gly Gly Asp Tyr Leu Ala Glu Tyr His Gly Gly
1               5                   10

<210> SEQ ID NO 34
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

Gly Tyr Glu Arg Pro Gly Trp Lys Leu Ser Gly
1               5                   10

<210> SEQ ID NO 35
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

Gly Gly Pro Ala Pro Ala Trp Ala His Gly Gly
1               5                   10

<210> SEQ ID NO 36
<211> LENGTH: 11
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 36

Gly Asn Ser Phe Asp Glu Trp Leu Gln Lys Gly
1               5                   10

<210> SEQ ID NO 37
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Any of the 20 natural amino acids
<220> FEATURE:
<221> NAME/KEY: MOD_RES
<222> LOCATION: (2)..(2)
<223> OTHER INFORMATION: Any of the 20 natural amino acids
<220> FEATURE:
<221> NAME/KEY: MOD_RES
<222> LOCATION: (8)..(8)
<223> OTHER INFORMATION: Any of the 20 natural amino acids
<220> FEATURE:
<221> NAME/KEY: MOD_RES
<222> LOCATION: (9)..(9)
<223> OTHER INFORMATION: Any of the 20 natural amino acids

<400> SEQUENCE: 37

Xaa Xaa Leu Ala Glu Tyr His Xaa Xaa
1               5

<210> SEQ ID NO 38
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Any of the 20 natural amino acids
<220> FEATURE:
<221> NAME/KEY: MOD_RES
<222> LOCATION: (2)..(2)
<223> OTHER INFORMATION: Any of the 20 natural amino acids
<220> FEATURE:
<221> NAME/KEY: MOD_RES
<222> LOCATION: (8)..(8)
<223> OTHER INFORMATION: Any of the 20 natural amino acids
<220> FEATURE:
<221> NAME/KEY: MOD_RES
<222> LOCATION: (9)..(9)
<223> OTHER INFORMATION: Any of the 20 natural amino acids

<400> SEQUENCE: 38

Xaa Xaa Arg Pro Gly Trp Lys Xaa Xaa
1               5

<210> SEQ ID NO 39
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
```

```
<221> NAME/KEY: MOD_RES
<222> LOCATION: (1)..(1)
<223> OTHER INFORMATION: Any of the 20 natural amino acids
<220> FEATURE:
<221> NAME/KEY: MOD_RES
<222> LOCATION: (2)..(2)
<223> OTHER INFORMATION: Any of the 20 natural amino acids
<220> FEATURE:
<221> NAME/KEY: MOD_RES
<222> LOCATION: (8)..(8)
<223> OTHER INFORMATION: Any of the 20 natural amino acids
<220> FEATURE:
<221> NAME/KEY: MOD_RES
<222> LOCATION: (9)..(9)
<223> OTHER INFORMATION: Any of the 20 natural amino acids

<400> SEQUENCE: 39

Xaa Xaa Pro Ala Trp Ala His Xaa Xaa
1               5

<210> SEQ ID NO 40
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Any of the 20 natural amino acids
<220> FEATURE:
<221> NAME/KEY: MOD_RES
<222> LOCATION: (2)..(2)
<223> OTHER INFORMATION: Any of the 20 natural amino acids
<220> FEATURE:
<221> NAME/KEY: MOD_RES
<222> LOCATION: (8)..(8)
<223> OTHER INFORMATION: Any of the 20 natural amino acids
<220> FEATURE:
<221> NAME/KEY: MOD_RES
<222> LOCATION: (9)..(9)
<223> OTHER INFORMATION: Any of the 20 natural amino acids

<400> SEQUENCE: 40

Xaa Xaa Phe Asp Glu Trp Leu Xaa Xaa
1               5

<210> SEQ ID NO 41
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Lys or Ile

<400> SEQUENCE: 41

Arg Ser Xaa Leu Tyr
1               5

<210> SEQ ID NO 42
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 42
```

```
Gly Asn Gly Phe Glu Val Tyr Leu Pro Gly Gly
1               5                   10

<210> SEQ ID NO 43
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 43

Gly Ser Glu Trp Thr Val Tyr Ala Gly Asn Gly
1               5                   10

<210> SEQ ID NO 44
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 44

Gly Ser Cys Arg Ser Ile Leu Tyr Gly Gln Gly
1               5                   10

<210> SEQ ID NO 45
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Any of the 20 natural amino acids
<220> FEATURE:
<221> NAME/KEY: MOD_RES
<222> LOCATION: (2)..(2)
<223> OTHER INFORMATION: Any of the 20 natural amino acids
<220> FEATURE:
<221> NAME/KEY: MOD_RES
<222> LOCATION: (8)..(8)
<223> OTHER INFORMATION: Any of the 20 natural amino acids
<220> FEATURE:
<221> NAME/KEY: MOD_RES
<222> LOCATION: (9)..(9)
<223> OTHER INFORMATION: Any of the 20 natural amino acids

<400> SEQUENCE: 45

Xaa Xaa Phe Glu Val Tyr Leu Xaa Xaa
1               5

<210> SEQ ID NO 46
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Any of the 20 natural amino acids
<220> FEATURE:
<221> NAME/KEY: MOD_RES
<222> LOCATION: (2)..(2)
<223> OTHER INFORMATION: Any of the 20 natural amino acids
<220> FEATURE:
```

```
<221> NAME/KEY: MOD_RES
<222> LOCATION: (8)..(8)
<223> OTHER INFORMATION: Any of the 20 natural amino acids
<220> FEATURE:
<221> NAME/KEY: MOD_RES
<222> LOCATION: (9)..(9)
<223> OTHER INFORMATION: Any of the 20 natural amino acids

<400> SEQUENCE: 46

Xaa Xaa Trp Thr Val Tyr Ala Xaa Xaa
1               5

<210> SEQ ID NO 47
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Any of the 20 natural amino acids
<220> FEATURE:
<221> NAME/KEY: MOD_RES
<222> LOCATION: (2)..(2)
<223> OTHER INFORMATION: Any of the 20 natural amino acids
<220> FEATURE:
<221> NAME/KEY: MOD_RES
<222> LOCATION: (8)..(8)
<223> OTHER INFORMATION: Any of the 20 natural amino acids
<220> FEATURE:
<221> NAME/KEY: MOD_RES
<222> LOCATION: (9)..(9)
<223> OTHER INFORMATION: Any of the 20 natural amino acids

<400> SEQUENCE: 47

Xaa Xaa Trp Glu Val His Leu Xaa Xaa
1               5

<210> SEQ ID NO 48
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Any of the 20 natural amino acids
<220> FEATURE:
<221> NAME/KEY: MOD_RES
<222> LOCATION: (2)..(2)
<223> OTHER INFORMATION: Any of the 20 natural amino acids
<220> FEATURE:
<221> NAME/KEY: MOD_RES
<222> LOCATION: (8)..(8)
<223> OTHER INFORMATION: Any of the 20 natural amino acids
<220> FEATURE:
<221> NAME/KEY: MOD_RES
<222> LOCATION: (9)..(9)
<223> OTHER INFORMATION: Any of the 20 natural amino acids

<400> SEQUENCE: 48

Xaa Xaa Arg Ser Ile Leu Tyr Xaa Xaa
1               5

<210> SEQ ID NO 49
<211> LENGTH: 5
<212> TYPE: PRT
<213> ORGANISM: Artificial Sequence
<220> FEATURE:
```

```
<223> OTHER INFORMATION: Description of Artificial Sequence: Synthetic
      peptide

<400> SEQUENCE: 49

Met Met Met Met Met
1               5

<210> SEQ ID NO 50
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 50

Ala Met Met Met Met
1               5

<210> SEQ ID NO 51
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 51

Pro Met Met Met Met
1               5

<210> SEQ ID NO 52
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 52

Val Met Met Met Met
1               5

<210> SEQ ID NO 53
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 53

Gln Met Met Met Met
1               5

<210> SEQ ID NO 54
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 54

Met Ala Met Met Met
1               5
```

-continued

```
<210> SEQ ID NO 55
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 55

Met Gln Met Met Met
1               5

<210> SEQ ID NO 56
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 56

Met Pro Met Met Met
1               5

<210> SEQ ID NO 57
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 57

Met Asn Met Met Met
1               5

<210> SEQ ID NO 58
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 58

Pro Ala Met Met Met
1               5

<210> SEQ ID NO 59
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 59

Pro Phe Met Met Met
1               5

<210> SEQ ID NO 60
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 60
```

```
Pro Val Met Met Met
1               5

<210> SEQ ID NO 61
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 61

Pro Glu Met Met Met
1               5

<210> SEQ ID NO 62
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 62

Val Ala Met Met Met
1               5

<210> SEQ ID NO 63
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 63

Val Phe Met Met Met
1               5

<210> SEQ ID NO 64
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 64

Val Glu Met Met Met
1               5

<210> SEQ ID NO 65
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 65

Ala Ala Met Met Met
1               5

<210> SEQ ID NO 66
<211> LENGTH: 5
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 66

Ala Phe Met Met Met
1               5

<210> SEQ ID NO 67
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 67

Ala Val Met Met Met
1               5

<210> SEQ ID NO 68
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 68

Ala Glu Met Met Met
1               5

<210> SEQ ID NO 69
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 69

Met Met Met Met
1

<210> SEQ ID NO 70
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Any of the 20 natural amino acids

<400> SEQUENCE: 70

Xaa Met Met Met Met Met
1               5

<210> SEQ ID NO 71
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
```

```
<222> LOCATION: (2)..(2)
<223> OTHER INFORMATION: Any of the 20 natural amino acids

<400> SEQUENCE: 71

Met Xaa Met Met Met Met
1               5

<210> SEQ ID NO 72
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Any of the 20 natural amino acids

<400> SEQUENCE: 72

Met Met Xaa Met Met Met
1               5

<210> SEQ ID NO 73
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Any of the 20 natural amino acids

<400> SEQUENCE: 73

Met Met Met Xaa Met Met
1               5

<210> SEQ ID NO 74
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: Any of the 20 natural amino acids

<400> SEQUENCE: 74

Met Met Met Met Xaa Met
1               5

<210> SEQ ID NO 75
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Any of the 20 natural amino acids

<400> SEQUENCE: 75

Met Met Met Met Met Xaa
1               5
```

```
<210> SEQ ID NO 76
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Asn or Phe

<400> SEQUENCE: 76

His Pro Gln Xaa
1

<210> SEQ ID NO 77
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Any of the 20 natural amino acids
<220> FEATURE:
<221> NAME/KEY: MOD_RES
<222> LOCATION: (2)..(2)
<223> OTHER INFORMATION: Any of the 20 natural amino acids
<220> FEATURE:
<221> NAME/KEY: MOD_RES
<222> LOCATION: (6)..(6)
<223> OTHER INFORMATION: Any of the 20 natural amino acids
<220> FEATURE:
<221> NAME/KEY: MOD_RES
<222> LOCATION: (7)..(7)
<223> OTHER INFORMATION: Any of the 20 natural amino acids

<400> SEQUENCE: 77

Xaa Xaa His Pro Gln Xaa Xaa
1               5

<210> SEQ ID NO 78
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Gln, Glu or Thr
<220> FEATURE:
<221> NAME/KEY: MOD_RES
<222> LOCATION: (4)..(4)
<223> OTHER INFORMATION: Tyr or His
<220> FEATURE:
<221> NAME/KEY: MOD_RES
<222> LOCATION: (5)..(5)
<223> OTHER INFORMATION: Leu, Ala, Val or Ile

<400> SEQUENCE: 78

Trp Xaa Val Xaa Xaa
1               5

<210> SEQ ID NO 79
<211> LENGTH: 5
<212> TYPE: PRT
```

```
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Phe, Leu or Tyr
<220> FEATURE:
<221> NAME/KEY: MOD_RES
<222> LOCATION: (2)..(2)
<223> OTHER INFORMATION: Gln, Glu or Thr
<220> FEATURE:
<221> NAME/KEY: MOD_RES
<222> LOCATION: (5)..(5)
<223> OTHER INFORMATION: Leu, Ile, Ala or Val

<400> SEQUENCE: 79

Xaa Xaa Val Tyr Xaa
1               5

<210> SEQ ID NO 80
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Gln, Glu or Thr
<220> FEATURE:
<221> NAME/KEY: MOD_RES
<222> LOCATION: (5)..(5)
<223> OTHER INFORMATION: Leu or Ile

<400> SEQUENCE: 80

Phe Xaa Val Tyr Xaa
1               5

<210> SEQ ID NO 81
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Gln, Glu or Thr
<220> FEATURE:
<221> NAME/KEY: MOD_RES
<222> LOCATION: (4)..(4)
<223> OTHER INFORMATION: Tyr or His
<220> FEATURE:
<221> NAME/KEY: MOD_RES
<222> LOCATION: (5)..(5)
<223> OTHER INFORMATION: Leu, Ala or Val

<400> SEQUENCE: 81

Trp Xaa Val Xaa Xaa
1               5

<210> SEQ ID NO 82
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
```

```
<221> NAME/KEY: MOD_RES
<222> LOCATION: (2)..(2)
<223> OTHER INFORMATION: Ser or Phe
<220> FEATURE:
<221> NAME/KEY: MOD_RES
<222> LOCATION: (4)..(4)
<223> OTHER INFORMATION: Leu or Val

<400> SEQUENCE: 82

Glu Xaa Thr Xaa Tyr
1               5

<210> SEQ ID NO 83
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 83

Phe Glu Val Tyr Leu Pro
1               5

<210> SEQ ID NO 84
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 84

Trp Thr Val Tyr Ala Gly
1               5

<210> SEQ ID NO 85
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 85

Cys Arg Ser Ile Leu Tyr
1               5
```

SYSTEMATIC DISCOVERY, MATURATION AND EXTENSION OF PEPTIDE BINDERS TO PROTEINS

SEQUENCE LISTING

The instant application contains a Sequence Listing which has been submitted electronically in ASCII format and is hereby incorporated by reference in its entirety. Said ASCII copy, created on May 11, 2020, is named 124009-0207 SL.txt and is 22,715 bytes in size.

BACKGROUND OF THE INVENTION

Understanding protein-protein interactions is important for basic research as well as various biomedical and other practical applications. Examples of this kind include binding between peptide fragments or epitopes and antibodies, the interaction between proteins and short fragments of other proteins, for example, MDM2 and p53 transactivation domain, Bcl-xL and Bak peptide, as well as binding between peptides referred to as aptamers to their target proteins. Development of simple and reliable methods of identifying peptide binders for proteins would help to understand the mechanisms of protein-protein interaction and open new opportunities for drug discovery.

State of the art in silico peptide discovery is guided by the X-ray crystal structures and relies on existing structural information. The application of such methods to de novo discovery of peptide binders is limited. To date, experimental methods provided the most effective approaches for peptide discovery. The commonly used methods rely on combinatorial peptide libraries in which peptides are linked to DNA or RNA molecules encoding them. The libraries are panned against immobilized target protein to identify most specific and tight binding peptides. Selection procedure performed in several rounds and after each round selected peptides are identified by PCR amplification of the encoding nucleic acid sequences. Different variations of this approach have been developed and successfully applied to peptide discovery; the most commonly used are phage display, ribosome display, and mRNA-display methods. Despite the unquestionable success of these methods at identifying peptide binders, they are expensive, time consuming and prone to contamination. Furthermore, the existing methods do not ensure that the top selected peptide binders are indeed the best binders and whether they can be improved. Currently, there is no systematic approach to this problem and laborious trial and error optimization techniques are used.

Another powerful experimental method to study peptide-protein interactions are peptide arrays. Peptide arrays could be made off peptides synthesized using solid phase peptide synthesis and then immobilized on solid support or could be directly prepared by in situ synthesis methods. Although peptide arrays are commercially available, their application is limited by a relatively low density and high cost of manufacturing. Both of these issues can be addressed by use of maskless light-directed technology, see (Pellois, Zhou et al. (2002) *Individually addressable parallel peptide synthesis on microchips*.) and U.S. Pat. No. 6,375,903.

Using a MAS instrument, the selection of nucleic acid or peptide sequences to be constructed on the microarray is under software control such that it is now possible to create individually-customized arrays based on the particular needs of an investigator. In general, MAS-based microarray synthesis technology allows for the parallel synthesis of millions of unique oligonucleotide or peptide features in a very small area of a standard microscope slide. The microarrays are generally synthesized by using light to direct which oligonucleotides or peptides are synthesized at specific locations on an array, these locations being called features.

One application of specific peptide binders is medical diagnostics. Prostate cancer is the most commonly diagnosed form of cancer in American men over the age of 50. Currently, the standard for detection of prostate cancer involves screening blood for levels of prostate specific antigen (PSA), digital-rectal examination, and needle biopsy of the prostate. PSA levels, however, may be compromised by variations in the amount of PSA produced by benign prostatic tissue (see, for example, Brawer M K, CA Cancer J Clin 49:264-281 (1999)). Thus, current PSA assays (and PSA alone) are not perfect for identifying prostate cancer (for and distinguishing it from benign hyperplasia. Thus, there is a need to identify means of more specifically targeting PSA and possibly additional biomarkers to improve diagnostic accuracy.

As noted above, the precise detection and identification of biologically relevant molecules within samples of interest is also important in the field of drug discovery. There exists an unmet need for a more efficient and successful method of identifying therapeutic candidates for existing and potential new targets, including targets that are presently considered "undruggable."

SUMMARY OF THE INVENTION

The instant disclosure provides systems and methods for identifying novel peptide binders for protein targets. According to some embodiments, the systems and methods disclosed herein identify peptide binders through identification of overlapping binding of the target protein to a small peptides comprising a comprehensive population of peptides immobilized on a microarray, then performing an exhaustive peptide maturation of the isolated core hit peptide binder, followed by N-terminal and C-terminal extension procedures. In some embodiments, the extended-mature core hit peptide may be subjected to further maturation processes and a new series of N-terminal and C-terminal extension processes.

In other embodiments, the invention provides novel peptide binders for prostate specific antigen (PSA), as well as systems, kits and methods of using the novel peptide binders for PSA in diagnosing, treating and monitoring prostate cancer in humans.

In yet another example, the invention provides novel peptide bingers for streptavidin, as well as systems, kits and methods of using the novel peptide binders for streptavidin in any in vitro or in vivo procedure where streptavidin is used or its detection, quantification or localization is desired.

In one embodiment, the invention is a peptide microarray comprising: a solid support having a reactive surface; and a population of peptides immobilized to the reactive surface, each peptide of the population of peptides comprising an amino acid sequence of interest. In some embodiments, the solid support is selected from plastic, glass and carbon composite. In some embodiments the reactive surface comprises an activated amine. In some embodiments, the amino acid sequence of interest of each peptide of the population of peptides comprises the same number of amino acids, e.g., five amino acids. In some embodiments, the amino acid sequence of interest does not contain any methionine, and/or cysteine amino acids and/or does not contain any amino acids repeats of the same amino acid, and/or does not contain any amino acid motifs consisting of a histidine (H)-proline (P)-glutamine (Q) sequence (SEQ ID NO: 13). In some embodiments, each peptide of the population of peptides further comprises at least one of a N-terminal and a C-terminal wobble synthesis oligopeptide. In some embodiments, one or both of the N-terminal and the C-terminal wobble synthesis oligopeptide comprises an amino acid sequence having the same number of amino acids, e.g., five, or more than five or less than five amino acids. In some embodiments, one or both of the C-terminal and N-terminal wobble synthesis oligopeptide wobble synthesis oligopeptide of each peptide is derived randomly from an amino acid mixture having each of the twenty amino acids in approximately equal concentrations, or from an amino acid mixture having amino acids glycine (G), serine (S), adenine (A), valine (V), aspartic acid (D), proline (P), glutamic acid (E), leucine (L), threonine (T) in approximately equal concentrations, or from an amino acid mixture having amino acids leucine (L), adenine (A), aspartic acid (D), lysine (K), threonine (T), glutamine (Q), proline (P), phenylalanine (F), valine (V), tyrosine (Y) in approximately equal concentrations, or from an amino acid mixture having amino acids glycine (G) and serine (S) in approximately a 3 (G) to 1 (S) concentration. In some embodiments, the C-terminal wobble synthesis oligopeptide of each peptide of the population of peptides comprises an amino acid sequence having the same number of amino acids. In some embodiments, the C-terminal wobble synthesis oligopeptide of each peptide is derived randomly from an amino acid mixture having each of the twenty amino acids in approximately equal concentrations, or from an amino acid mixture having amino acids glycine (G), serine (S), adenine (A), valine (V), aspartic acid (D), proline (P), glutamic acid (E), leucine (L), threonine (T) in approximately equal concentrations, or from an amino acid mixture having amino acids leucine (L), adenine (A), aspartic acid (D), lysine (K), threonine (T), glutamine (Q), proline (P), phenylalanine (F), valine (V), tyrosine (Y) in approximately equal concentrations, or from an amino acid mixture having amino acids glycine (G) and serine (S) in approximately a 3 (G) to 1 (S) concentration.

In another embodiment, the invention is a method of identifying a peptide binder comprising the steps of: exposing a protein target of interest, to an array comprising a first population of peptide binders, whereby the protein target binds to at least one peptide binder comprising the population; identifying overlap in peptide binder sequences comprising the population which bind the protein target of interest, whereby a core binder sequence is determined; performing at least one alteration selected from a single amino acid substitution, a double amino acid substitution, an amino acid deletion, and an amino acid insertion of amino acids comprising the core binder sequence, whereby a second population of core binder sequences is generated; exposing the second population to the protein target, whereby the protein target binds to at least one peptide sequence of the second population; identifying one or more sequences of the second population demonstrating strong binding properties to the protein target, whereby a matured core binder sequence is determined; performing at least one of N-terminal and C-terminal extension of the matured core binder sequence determined in step e, whereby a population of matured extended peptide binders is generated; exposing the protein target of interest to an array comprising the population of matured peptide binders generated in step f; and identifying overlap in the N-terminal or C-terminal peptide binder sequences of the peptides comprising the population of mature peptide binders, whereby an extended, matured core peptide binder sequence is determined. In variations of this embodiment, least one of a label-free and affinity analysis of the extended, matured core peptide binder sequence is performed. In some embodiments, the protein target is an enzyme, for example, a sortase, a protease, a kinase, a phosphatase, a BirA biotinylation enzyme, a ligase, a lipase, a phosphodiesterase, a collagenase, a hydrolase, and an esterase.

In variations of this embodiment, the array comprises at least one of glass, plastic, and carbon composite. In some variations of this embodiment, the peptide binders of the first population comprise the same number of amino acids. In other variations of this embodiment, the peptide binders of the first population do not include the amino acid cysteine or methionine, or histidine-proline-glutamine motifs (SEQ ID NO: 13), or amino acid repeats of 2 or more amino acids. In further variations of this embodiment, the peptide binders of the population of matured extended peptide binders include at least one of N-terminal and C-terminal wobble synthesis. In other variations of this embodiment, the core binder sequence comprises a greater number of amino acids than the number of amino acids for each of the peptides comprising the first population of peptide binders. In other variations of this embodiment, the peptides are identified via principled clustering analysis.

In other embodiments, the invention is a method of diagnosing prostate cancer using a peptide binder. According to some embodiments, a patient's sample is exposed to one or more peptide binder disclosed herein. In some embodiments, the peptide binder is comprises a label detectable by e.g., immunohistochemistry, in-situ hybridization, PCR or chromatography. In variations of this embodiment, a chromatography column comprising one or more peptide binder disclosed herein is used and a sample containing PSA is passed over the column.

In another embodiment, the invention is an artificial polypeptide with specific affinity to prostate specific antigen (PSA), consisting of an amino acid sequence that is at least 80% homologous to a sequence selected from the group consisting of SEQ ID NO: 1-12.

In another embodiment, the invention is a method of diagnosing prostate cancer in a subject comprising: contacting a sample from the subject with a peptide binder comprising an amino acid sequence at least 80% homologous to the amino acid sequence selected from the group consisting of SEQ ID NO: 1-12 and having a detectable label; detecting a signal from the label proportional to the amount of PSA in the sample, whereby a concentration of PSA in the sample is calculated; comparing the concentration of PSA in the sample to a reference value; and providing a diagnosis of prostate cancer in the subject if the concentration of PSA in the sample is greater than the PSA reference value.

In another embodiment, the invention is a method of treating prostate cancer comprising administering to a subject a pharmaceutically effective amount of a compound comprising a peptide binder comprising an amino acid sequence at least 80% homologous to the amino acid sequence selected from the group consisting of SEQ ID NO. 1-12.

In another embodiment, the invention is a kit comprising at least one peptide binder comprising an amino acid sequence at least 80% homologous to the amino acid sequence selected from the group consisting of SEQ ID NO. 1-12.

In another embodiment, the invention is an artificial polypeptide with specific affinity to streptavidin, consisting of an amino acid sequence that is at least 80% homologous to a sequence selected from the group consisting of SEQ ID NO: 13-27.

In some embodiments, the invention is a method of detecting a presence of streptavidin in a sample, the method comprising: contacting the sample with a peptide binder comprising an amino acid sequence at least 80% homologous to the amino acid sequence selected from the group consisting of SEQ ID NO: 13-27 and having a detectable label; detecting a signal from the label indicating the presence or amount of streptavidin in the sample. In some embodiments, streptavidin in the sample is present within a streptavidin-biotin complex. In other embodiments, streptavidin in the sample is present in the form of a streptavidin fragment.

In another embodiment, the invention is a kit comprising at least one peptide binder comprising an amino acid sequence at least 80% homologous to the amino acid sequence selected from the group consisting of SEQ ID NO.13-27.

DETAILED DESCRIPTION OF THE INVENTION

Figure 1:
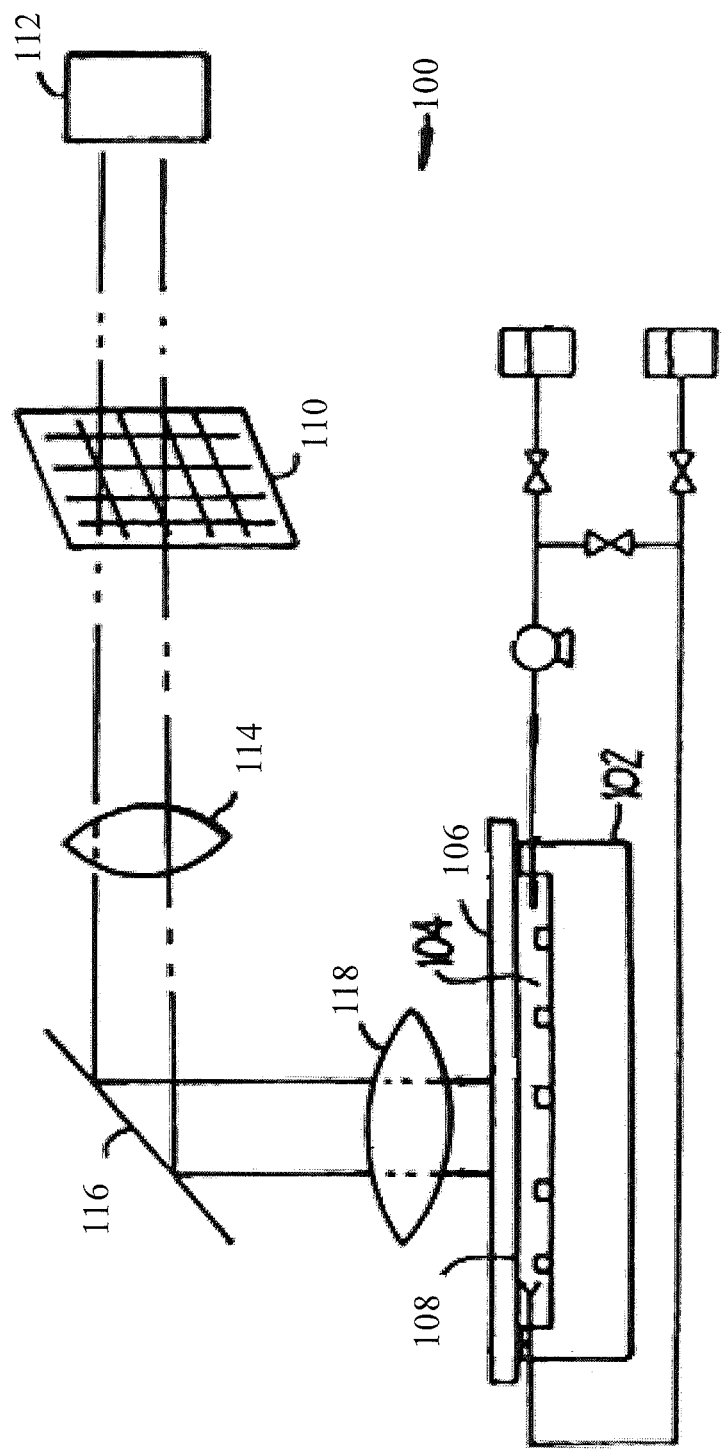
FIG. 1 is a schematic view of a microarray system for array synthesis by way of a photolithographic technique utilizing photolithographic mask (Prior art).

The instant disclosure provides systems and methods by which novel peptide binders to proteins can be synthesized, optimized and identified. Embodiments of the instant disclosure also include novel components and kits of the systems disclosed herein, and novel methods by which such components are generated and utilized.

I. Peptides:

According to various embodiments of the instant disclosure, novel peptides are disclosed. The peptides disclosed and described herein make up a class of molecules having a vast number of applications in the life science and healthcare fields. As disclosed and described herein, the peptides (or "peptide binders") presented herein may be in a linear, cyclic or constrained (macrocycle) form.

As used herein, the terms "peptide," "oligopeptide" or "peptide binder" refer to organic compounds composed of amino acids, which may be arranged in either a linear chain (joined together by peptide bonds between the carboxyl and amino groups of adjacent amino acid residues), in a cyclic form or in a constrained (e.g., "macrocycle" form). The terms "peptide" or "oligopeptide" also refer to shorter polypeptides, i.e., organic compounds composed of less than 50 amino acid residues. A macrocycle (or constrained peptide), as used herein, is used in its customary meaning for describing a cyclic small molecule such as a peptide of about 500 Daltons to about 2,000 Daltons.

The term "natural amino acid" refers to one of the 20 amino acids typically found in proteins and used for protein biosynthesis as well as other amino acids which can be incorporated into proteins during translation (including pyrrolysine and selenocysteine). The 20 natural amino acids include histidine, alanine, valine, glycine, leucine, isoleucine, aspartic acid, glutamic acid, serine, glutamine, asparagine, threonine, arginine, proline, phenylalanine, tyrosine, tryptophan, cysteine, methionine and lysine.

The term "non-natural amino acid" refers to an organic compound that is not among those encoded by the standard genetic code, or incorporated into proteins during translation. Therefore, non-natural amino acids include amino acids or analogs of amino acids, but are not limited to, the D-isostereomers of amino acids, the beta-amino-analogs of amino acids, citrulline, homocitrulline, homoarginine, hydroxyproline, homoproline, ornithine, 4-amino-phenylalanine, cyclohexylalanine, α-aminoisobutyric acid, N-methyl-alanine, N-methyl-glycine, norleucine, N-methyl-glutamic acid, tert-butylglycine, α-aminobutyric acid, tert-butylalanine, 2-aminoisobutyric acid, α-aminoisobutyric acid, 2-aminoindane-2-carboxylic acid, selenomethionine, dehydroalanine, lanthionine, γ-amino butyric acid, and derivatives thereof wherein the amine nitrogen has been mono- or di-alkylated.

According to embodiments of the instant disclosure, novel peptide binders are presented which are immobilized on a support surface (e.g., a microarray). As described in greater detail below, the peptide binders in enabling discovery techniques such as profiling of antibodies, epitope identification, sample profiling, antibody isolation, protein identification as well as diagnostic applications. Furthermore, embodiments of the peptide binders can be extended and matured (for example, to a cyclic peptide with non-natural amino acids) for preparing a potential drug candidate.

Some embodiments of the instant disclosure include novel methods of synthesis of the peptides presented herein. Current methods of synthesizing the peptides, such as macrocycles, include chemical means or utilization of ribosomal translation system (either in vivo or in vitro). Other embodiments of the instant disclosure include the synthesis of arrays by various methods, including by way of maskless array synthesis which enables ultra-high density synthesis of up to 2.9 million unique peptides.

II. Microarrays:

According to embodiments of the instant disclosure, oligopeptide microarrays are presented which may be used in research and healthcare. For example, embodiments of instant oligopeptide arrays may be utilized in the identification of biologically active motifs (e.g., oligopeptide microarrays may imitate potential active motifs of ligands for screening the binding to corresponding receptors). Furthermore, the oligopeptide microarrays disclosed herein might reflect specific sequences of disease-associated antigens (and thus be utilized for diagnostic or monitoring purposes, e.g., to detect antibodies from patient samples suggesting the presence of certain inflammatory diseases and infections). Another application of the oligopeptide microarrays is the discovery of biochemical interactions, including the binding of proteins or DNA to oligopeptides probes immobilized on an array. In addition to the other numerous functions disclosed and described herein, oligopeptide microarrays can further be used for profiling cellular activity, enzymatic activity, cell adhesion, and the like.

Various methods for the production of oligopeptide microarrays are known in the art. For example, spotting prefabricated peptides or in-situ synthesis by spotting reagents, e.g., on membranes, exemplify known methods. Other known methods used for generating peptide arrays of higher density are the so-called photolithographic techniques, where the synthetic design of the desired biopolymers is controlled by suitable photolabile protecting groups (PLPG) releasing the linkage site for the respective next component (amino acid, oligonucleotide) upon exposure to electromagnetic radiation, such as light (Fodor et al., (1993) *Nature* 364:555-556; Fodor et al., (1991) *Science* 251:767-773). Two different photolithographic techniques are known in the state of the art. The first is a photolithographic mask, used to direct light to specific areas of the synthesis surface effecting localized deprotection of the PLPG (see, for example, FIG. 1). "Masked" methods include the synthesis of polymers utilizing a mount (e.g., a "mask") which engages a substrate and provides a reactor space between the substrate and the mount. Exemplary embodiments of such "masked" array synthesis are described in, for example, U.S. Pat. Nos. 5,143,854 and 5,445,934, the disclosures of which are hereby incorporated by reference. Potential drawbacks of this technique, however, include the need for a large number of masking steps resulting in a relatively low overall yield and high costs, e.g., the synthesis of a peptide of only six amino acids in length could require over 100 masks. The second photolithographic technique is the so-called maskless photolithography, where light is directed to specific areas of the synthesis surface effecting localized deprotection of the PLPG by digital projection technologies, such as micromirror devices (Singh-Gasson et al., *Nature Biotechn.* 17 (1999) 974-978). Such "maskless" array synthesis thus eliminates the need for time-consuming and expensive production of exposure masks. It should be understood that the embodiments of the systems and methods disclosed herein may comprise or utilize any of the various array synthesis techniques described above.

The use of PLPG (photolabile protecting groups), providing the basis for the photolithography based synthesis of oligopeptide microarrays, is well known in the art. Commonly used PLPG for photolithography based biopolymer synthesis are for example a-methyl-6-nitropiperonyl-oxycarbonyl (MeNPOC) (Pease et al., *Proc. Natl. Acad. Sci. USA* (1994) 91:5022-5026), 2-(2-nitrophenyl)-propoxycarbonyl (NPPOC) (Hasan et al. (1997) *Tetrahedron* 53: 4247-4264), nitroveratryloxycarbonyl (NVOC) (Fodor et al. (1991) *Science* 251:767-773) and 2-nitrobenzyloxycarbonyl (NBOC) (Patchornik et al. (1970) 21:6333-6335).

Amino acids have been introduced in photolithographic solid-phase peptide synthesis of oligopeptide microarrays, which were protected with NPPOC as a photolabile amino protecting group, wherein glass slides were used as a support (U.S. App. Pub. No. 2005/0101763 A1). The method using NPPOC protected amino acids has the disadvantage that the half-life upon irradiation with light of all (except one) protected amino acids is within the range of approximately 2 to 3 minutes under certain conditions. In contrast, under the same conditions, NPPOC-protected tyrosine exhibits a half-life of almost 10 minutes. As the velocity of the whole synthesis process depends on the slowest sub-process, this phenomenon increases the time of the synthesis process by a factor of 3 to 4. Concomitantly, the degree of damage by photogenerated radical ions to the growing oligomers increases with increasing and excessive light dose requirement.

As used herein, the terms "microarray" or "oligopeptide microarray" refer to a two dimensional arrangement of features on the surface of a solid or semi-solid support. A single microarray or, in some cases, multiple microarrays (e.g., 3, 4, 5, or more microarrays) can be located on one solid support. The size of the microarrays depends on the number of microarrays on one solid support. The higher the number of microarrays per solid support, the smaller the arrays have to be to fit on the solid support. The arrays can be designed in any shape, but preferably they are designed as squares or rectangle. The ready to use product is the oligopeptide microarray on the solid or semi-solid support (microarray slide).

The term "peptide microarray" (or peptide chip or peptide epitope microarray) includes a population or collection of peptides displayed on a solid surface, for example a glass, carbon composite or plastic array, slide or chip. Exemplary uses of peptide microarrays include the fields of biology, medicine and pharmacology, including the study of binding properties, functionality and kinetics of protein-protein interactions. Basic research use may include profiling of enzymes (e.g., kinase, phosphatase, protease, acetyltransferase, histone deacetylase) and mapping an antibody epitope to find key residues for protein binding. Other applications include seromarker discovery, profiling of changing humoral immune responses of individual patients during disease progression, monitoring of therapeutic interventions, patient stratification and development of diagnostic tools and vaccines.

The term "feature" refers to a defined area on the surface of a microarray. The feature comprises biomolecules, such as peptides, nucleic acids, carbohydrates, and the like. One feature can contain biomolecules with different properties, such as different sequences or orientations, as compared to other features. The size of a feature is determined by two factors: i) the number of features on an array, the higher the number of features on an array, the smaller is each single feature, ii) the number of individually addressable aluminum mirror elements which are used for the irradiation of one feature. The higher the number of mirror elements used for the irradiation of one feature, the bigger is each single feature. The number of features on an array may be limited by the number of mirror elements (pixels) present in the micro mirror device. For example, the state of the art micro mirror device from Texas Instruments, Inc. currently contains 4.2 million mirror elements (pixels), thus the number of features within such exemplary microarray is therefore limited by this number. However, it should be understood that the micro mirror device from Texas Instruments, Inc. is provided only for exemplary purposes and higher density arrays are possible.

The term "solid or semi-solid support" refers to any solid material, having a surface area to which organic molecules can be attached through bond formation or absorbed through electronic or static interactions such as covalent bond or complex formation through a specific functional group. The support can be a combination of materials such as plastic on glass, carbon on glass, and the like. The functional surface can be simple organic molecules but can also comprise of co-polymers, dendrimers, molecular brushes and the like.

The term "plastic" refers to synthetic materials, such as homo- or hetero-co-polymers of organic building blocks (monomer) with a functionalized surface such that organic molecules can be attached through covalent bond formation or absorbed through electronic or static interactions such as through bond formation through a functional group. Preferably the term "plastic" refers to polyolefin, which is a polymer derived by polymerization of an olefin (e.g., ethylene propylene diene monomer polymer, polyisobutylene). Most preferably, the plastic is a polyolefin with defined optical properties, like TOPAS® or ZEONOR/EX®.

The term "functional group" refers to any of numerous combinations of atoms that form parts of chemical molecules, that undergo characteristic reactions themselves, and that influence the reactivity of the remainder of the molecule. Typical functional groups include, but are not limited to, hydroxyl, carboxyl, aldehyde, carbonyl, amino, azide, alkynyl, thiol and nitril. Potentially reactive functional groups include, for example, amines, carboxylic acids, alcohols, double bonds, and the like. Preferred functional groups are potentially reactive functional groups of amino acids such as amino groups or carboxyl groups.

As understood by one of skill in the art, peptide microarrays comprise an assay principle whereby thousands (or in the case of the instant disclosure, millions) of peptides (in some embodiments presented in multiple copies) are linked or immobilized to the surface of a solid support (which in some embodiments comprises a glass, carbon composite or plastic chip or slide). According to embodiments of the instant disclosure, peptide microarrays may be incubated with a variety of different biological samples including purified enzymes or antibodies, patient or animal sera, cell lysates, and the like. In particular, ligands for receptors or substrates for enzymes can be identified. For example, substrates for a sortase, a protease, a kinase, a phosphatase, a BirA biotinylation enzyme, a ligase, a lipase, a phosphodiesterase, a collagenase, a hydrolase, and an esterase may be identified using the method of the invention.

In some embodiments, the peptide microarray, after incubation with a sample of interest, undergoes one or more washing steps, and then is exposed to a secondary antibody having a desired specificity (e.g. anti IgG human/mouse or anti phosphotyrosine or anti myc). Usually, the secondary antibody is tagged by a fluorescence label that can be detected by a fluorescence scanner. Other detection methods are chemiluminescence, colorimetry or autoradiography.

After scanning the microarray slides, the scanner records a 20-bit, 16-bit or 8-bit numeric image in tagged image file format (*.tif). The .tif-image enables interpretation and quantification of each fluorescent spot on the scanned microarray slide. This quantitative data is the basis for performing statistical analysis on measured binding events or peptide modifications on the microarray slide. For evaluation and interpretation of detected signals an allocation of the peptide spot (visible in the image) and the corresponding peptide sequence has to be performed.

A peptide microarray is a slide with peptides spotted onto it or assembled directly on the surface by in-situ synthesis. Peptides are ideally covalently linked through a chemoselective bond leading to peptides with the same orientation for interaction profiling. Alternative procedures include unspecific covalent binding and adhesive immobilization.

Figure 2:
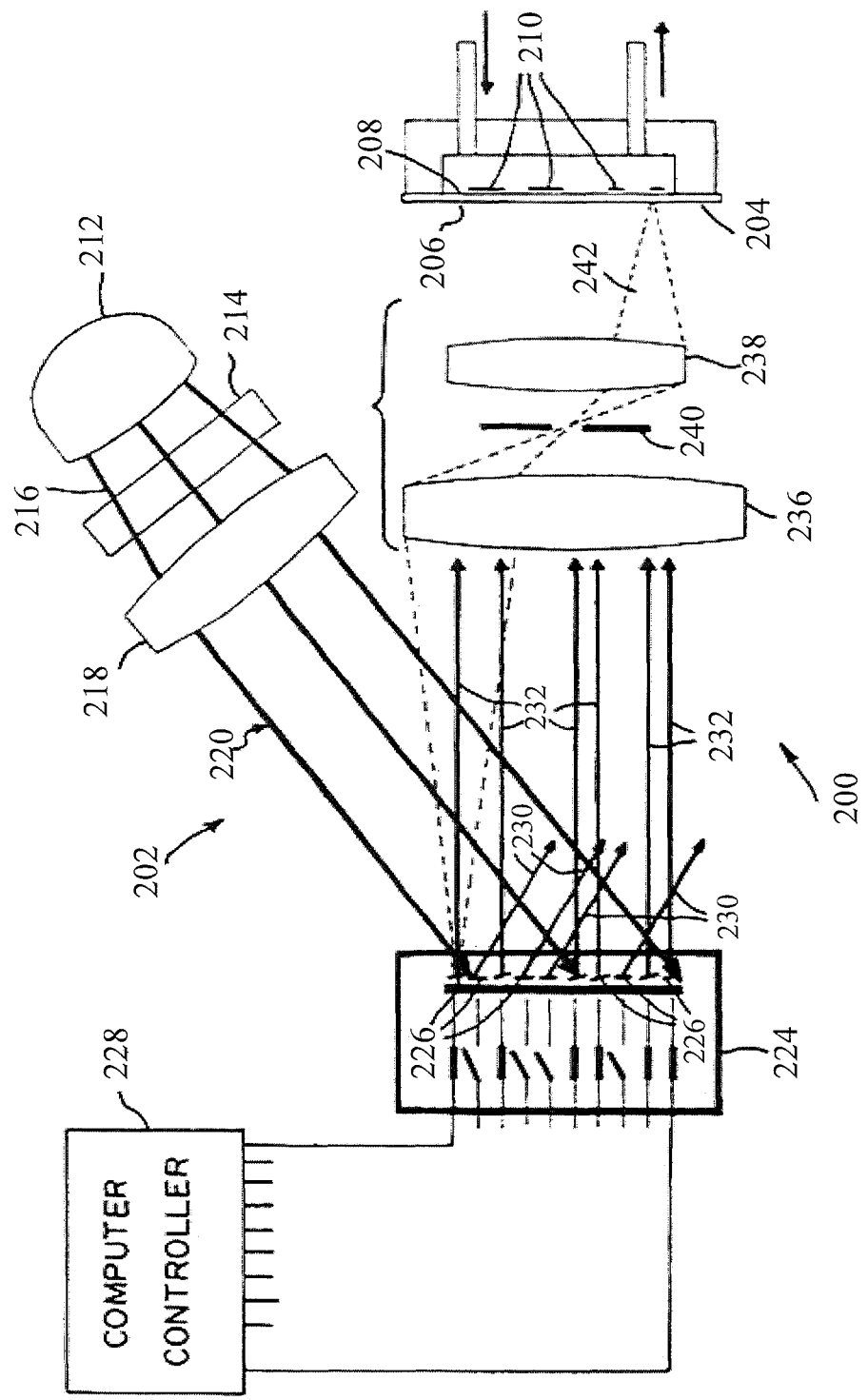
FIG. 2 is a schematic view of a microarray system for array synthesis by way of a photolithographic technique utilizing maskless photolithography (Prior art).

With reference to FIGS. 1 and 2, embodiments of various array synthesizers (utilized in both masked and maskless photolithographic techniques, respectively) are presented. Specifically referring now to FIG. 1, an exemplary system 100 for performing masked photolithographic techniques (such as taught in U.S. Pat. No. 5,445,934) is shown, illustrating a system body 102 with a cavity 104 defined at a surface thereof. A substrate (solid support) 106, having a photoremovable protective group (for example, such as NVOC with or without an intervening linker molecule) along its bottom surface 108 is mounted above the cavity 104. The substrate 106, for example, may be transparent to a wide spectrum of light, or in some embodiments is transparent only at a wavelength at which the protective group may be removed (such as UV in the case of NVOC). The substrate (solid support) 106 and the body 102 seal the cavity 104 (except for inlet and outlet ports) and may be mated, for example, by way of gasket(s) or a vacuum.

Lens 118, and in some embodiments, reflective mirror 116 are provided for focusing and directing light from light source 112 (such as a Xe(Hg) light source) onto substrate 106. In the illustrated embodiment of FIG. 1 a second lens 114 is shown (and in some embodiments may be provided) for projecting a mask image onto the substrate in combination with lens 118 (a.k.a., "projection printing"). Light (from light source 112), prior to contacting substrate 106 contacts mask 110, whereby such light is permitted to reach only selected locations on substrate 106. Mask 110 may be, for example, a glass slide having etched chrome thereon. In some embodiments, mask 110 may be provided with a grid of transparent locations and opaque locations, for example. As is understood by a person of skill in the art, with masked array synthesis, light passes freely through "transparent" regions of mask 110, but is reflected from, or absorbed by, other (e.g., "non-transparent") regions of mask 110. Thus, only selected regions of substrate 106 are exposed to light.

Also, light valves (LCD's) may be used as an alternative to conventional masks (to selectively expose regions of the substrate); fiberoptic faceplates may be used (for contrast enhancement of the mask or as the sole means of restricting the region to which light is applied); and fly's-eye lenses, tapered fiberoptic faceplates, or the like, may also be used for contrast enhancement. Also, it should be understood that illumination of regions smaller than a wavelength of light may be accomplished with more elaborate techniques as known in the art (e.g., directing light at the substrate by way of molecular microcrystals on the tip of, for example, micropipettes). Exemplary devices are disclosed in Lieberman et al., "A Light Source Smaller than the Optical Wavelength," Science (1990) 247:59-61.

Now, specifically referring to FIG. 2, an exemplary "maskless" array system (as described, for example, in U.S. Pat. No. 6,375,903) that may be utilized in accordance with the instant disclosure is provided for illustrating "maskless" DNA, peptide or the like, array synthesis. The illustrative system, shown generally as 200, is depicted including a two-dimensional array image former 202 and a substrate 204 onto which the array image is projected. In the illustrative embodiment presented at FIG. 2, the substrate has an exposed entrance surface 206 and an opposite active surface 208 on which a two-dimensional array of peptide sequence probes 210 are to be fabricated. However, in some embodiments the substrate 204 may have active surface 208 facing the image former 202 and enclosed within a reaction chamber flow cell having a transparent window (allowing light to be projected onto the active surface 208). Embodiments may include opaque or porous substrates 204 as well.

In some embodiments of maskless microarrays according to this instant disclosure, image former 202 may include a light source 212 (e.g., an ultraviolet or near ultraviolet source such as a mercury arc lamp), an optional filter 214 (to receive output beam 216 from source 212 and selectively pass only the desired wavelengths, e.g., 365 nm Hg line), and a condenser lens 218 (for forming a collimated beam 220). Other devices for filtering or monochromating the source light, e.g., diffraction gratings, dichroic mirrors, and prisms, may also be used rather than a transmission filter, and are generically referred to as "filters" herein.

As shown, beam 220 is projected a two-dimensional micromirror array device 224 having a two-dimensional array of individual micromirrors 226 which are each responsive to control signals (provided by computer controller 228) supplied to the array device 224 to tilt in one of at least two directions. In some embodiments, the micromirrors 226 are constructed so that: A.) in a first position beam 220 that strikes an individual micromirror 226 may be deflected in a direction oblique to beam 220 (as indicated by the arrows 230); and B.) In a second position, beam 220 striking such mirrors is reflected back parallel to beam 220, as indicated by the arrows 232. As should be understood, the light reflected from each of the mirrors 226 constitutes an individual beam 232. The beams 232 are incident upon projection optics 234 (comprising, for example, lenses 236, 238 and an adjustable iris 240). The projection optics 234 serve to form an image of the pattern of the micromirror array 224, as represented by the individual beams 232 (and the dark areas between these beams), on the active surface 208 of the substrate 204. As described above and throughout this disclosure, the substrate support 204 may be transparent, and may be, for example, formed of fused silica or soda lime glass or quartz, so that the light projected thereon (illustrated by the lines 242), passes through substrate 204 without substantial attenuation or diffusion.

An exemplary micromirror array 224 in accordance with the instant disclosure includes the Digital Micromirror Device (DMD) (available commercially from Texas Instruments, Inc.) which are capable of forming patterned beams of light by electronically addressing the micromirrors in the arrays. Such arrays are discussed, for example, in: Larry J. Hornbeck, "Digital Light Processing and MEMs: Reflecting the Digital Display Needs of the Networked Society," SPIE/EOS European Symposium on Lasers, Optics, and Vision for Productivity and Manufacturing I, Besancon, France, Jun. 10-14, 1996; and U.S. Pat. Nos. 5,096,279, 5,535,047, 5,583,688, 5,600,383 and 6.375,903. The micromirrors 226 of such devices are capable of reflecting the light of normal usable wavelengths, including ultraviolet and near ultraviolet light, in an efficient manner without damage to the mirrors themselves.

In some microarray embodiments, the projection optics 234 may be of standard design. Lenses 236, 238 focus the light in beam 232 (passed through adjustable iris 240) onto the active surface 208 of substrate 204. The iris 240 aides in controlling the effective numerical aperture and in ensuring that unwanted light (particularly the off-axis beams 230) are not transmitted to substrate 204. Resolutions of dimensions as small as a fraction of a micron are obtainable with such optics systems. Various alternate configurations (e.g., for example as preferred in manufacturing applications), as known in the art may also be utilized in accordance with the instant application.

It should be understood that although exemplary embodiments are provided herein, various approaches may be utilized in the fabrication of the peptide binder probes 210 on the substrate 204, and include adaptations of microlithographic techniques. For example, in a "direct photofabrication approach," the substrate 204 may be coated with a layer of a chemical capable of binding amino acids (e.g., an amine) which, for example, may be protected with a chemical group that is able to react with and be removed by light. Light therefore may be applied by the projection system 202, deprotecting the amine groups on the substrate 204 and making them available for binding the amino acids (which are flowed onto the active surface 208 of the substrate 204 for binding to the selected sites using normal chemistry). This process is repeated multiple times, thereby binding another amino acid to a different set of locations. The process is simple, and if a combinatorial approach is used the number of permutations increases exponentially.

According to some embodiments of the instant disclosure, maskless array synthesis is utilized in the fabrication of the peptide binder probes 210 on substrate 204. According to such embodiments, the maskless array synthesis employed allows ultra-high density peptide synthesis with synthesis up to 2.9M unique peptides. Each of 2.9M synthesis features/regions having up to 107 reactive sites that could yield a full length peptide. Smaller arrays can also be designed. For example, an array representing a comprehensive list of all possible 5-mer peptides using all natural amino acids excluding cysteine will have 2,476,099 peptides. An array of 5-mer peptides by using all combinations of 18 natural amino acids excluding cysteine and methionine may also be used. Additionally, an array can exclude other amino acids or aminoacid dimers. For example, the 18-mer array exemplified above may be designed to exclude any dimer or a longer repeat of the same amino acid, as well as any peptide containing HR, RH, HK, KH, RK, KR, HP, and PQ sequences to create a library of 1,360,732 unique peptides. Smaller arrays may have replicates of each peptide on the same array to increase the confidence of the conclusions drawn from array data.

In various embodiments, the peptide arrays described herein can have at least $1.6 \times 10^5$ peptides, at least $2.0 \times 10^5$ peptides, at least $3.0 \times 10^5$ peptides, at least $4.0 \times 10^5$ peptides, at least $5.0 \times 10^5$ peptides, at least $6.0 \times 10^5$ peptides, at least $7.0 \times 10^5$ peptides, at least $8.0 \times 10^5$ peptides, at least $9.0 \times 10^5$ peptides, at least $1.0 \times 10^6$ peptides, at least $1.2 \times 10^6$ peptides, at least $1.4 \times 10^6$ peptides, at least $1.6 \times 10^6$ peptides, at least $1.8 \times 10^6$ peptides, at least $1.0 \times 10^7$ peptides, or at least $1.0 \times 10^8$ peptides attached to the solid support of the peptide array. In other embodiments, the peptide arrays described herein can have about $1.6 \times 10^5$ peptides, about $2.0 \times 10^5$ peptides, about $3.0 \times 10^5$ peptides, about $4.0 \times 10^5$ peptides, about $5.0 \times 10^5$ peptides, about $6.0 \times 10^5$ peptides, about $7.0 \times 10^5$ peptides, about $8.0 \times 10^5$ peptides, about $9.0 \times 10^5$ peptides, about $1.0 \times 10^6$ peptides, about $1.2 \times 10^6$ peptides, about $1.4 \times 10^6$ peptides, about $1.6 \times 10^6$ peptides, about $1.8 \times 10^6$ peptides, about $1.0 \times 10^7$ peptides, or about $1.0 \times 10^8$ peptides attached to the solid support of the peptide array. As described herein, a peptide array comprising a particular number of peptides can mean a single peptide array on a single solid support, or the peptides can be divided and attached to more than one solid support to obtain the number of peptides described herein.

Arrays synthesized in accordance with such embodiments can be designed for peptide binder discovery in the linear or cyclic form (as noted herein) and with and without modification such as N-methyl or other PTMs. Arrays are also be designed for further extension of potential binders using a block-approach by performing iterative screens on the N-term and C-term of a potential hit (as is further described in detail herein). Once a hit of an ideal affinity has been discovery it can be further matured using a combination of maturation arrays (described further herein), that allow a combinatorial insertion, deletion and replacement analysis of various amino acids both natural and non-natural.

The peptide arrays of the instant disclosure can be used in monoclonal antibody cross reactivity profiling, polyclonal sera profiling, epitope identification (for an, antibody of interest), lupus immune reactivity profiling, gut profiling; cancer biomarker profiling, pseudo-monoclonal antibody isolation (from isolates of a polyclonal antibody), peptide to protein interaction characterization, affinity purification, specific and sensitive binding analysis for diagnostic applications. Additionally, peptide binders identified and disclosed herein (through the process disclosed herein) can be matured to a cyclic peptide (including with non-natural amino acids) making such binder a potential drug candidate.

Figure 3:
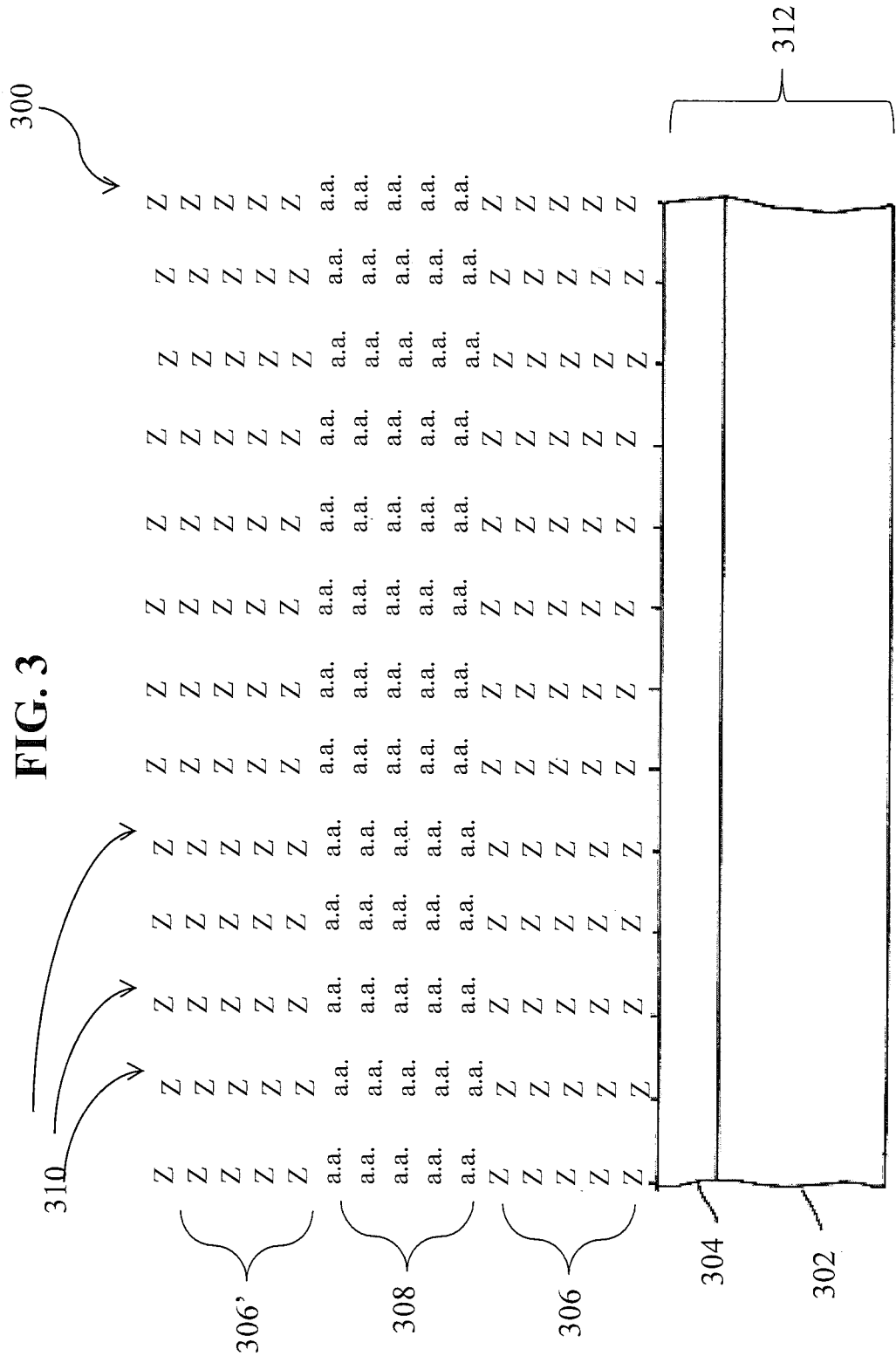
FIG. 3 is a schematic view illustrating arrays comprising peptide probes thereon in accordance with the present disclosure.

III. Peptide Binder Discovery:

Discovery of novel binders (see, for example, FIG. 4, the method generally represented as 400) may be accomplished, according to the instant disclosure. As explained herein, such novel binders can be utilized in numerous applications, including but not limited to therapeutics, diagnostic applications and general laboratory applications. According to some specific embodiments of the instant disclosure, a peptide array may be designed comprising a population of hundreds, thousands, tens of thousands, hundreds of thousands and even millions of peptides. With reference to FIG. 3, in some embodiments, the population of peptides 310 can be configured such that the peptides represent an entire protein, gene, chromosome, molecule or even and entire organism (e.g., a human) of interest. Additionally, the peptides can be configured according to specific criteria, whereby specific amino acids or motifs are excluded. Furthermore, the peptides can be configured such that each peptide comprises an identical length. For example, in some embodiments the population of peptides 310 immobilized on the array 312 may all comprise 3-, 4-, 5-, 6-, 7-, 8-, 9-, 10-, 11-, or even 12-mers, or more. In some embodiments, the peptides may also each comprise an N-terminal or a C-terminal sequence (for example, 306 and 306') where each peptide comprises both an N and a C terminal peptide sequence of a specific and identical length (e.g., 3-, 4-, 5-, 6-, 7- or even 8- or more peptides).

According to some embodiments, a peptide array 300 is designed including a population of up to 2.9 million peptides 310, configured such that the 2.9 million peptides represents a comprehensive list of all possible 5-mer peptides 308 of a genome, immobilized on an array 312. In some such embodiments, the 5-mer peptides 308 (comprising the 2.9 million peptides of the array) may exclude the amino acid cysteine (C) (in order to aide in controlling unusual folding of the peptide); or the amino acid methionine (M) (because M is considered a rare amino acid within the proteome); and/or all amino acid repeats of 2 or more of the same amino acid (in order to aide in controlling non-specific interactions such as charge and hydrophobic interactions); or amino acid motifs consisting of histidine (H)-proline (P)-glutamine (Q) sequence (which is a known streptavidin binding motif) (SEQ ID NO: 13). In some illustrative embodiments, such as provided at FIG. 3, the 5-mer peptides 308 may exclude one, or more than one of the exclusions listed above. One embodiment of the invention includes a peptide array comprising a population of up to 2.9 million 5-mer peptides 310, representing the entire human genome, wherein the 5-mer peptides 308 do not include any of the amino acids C and M, do not include amino acid repeats of 2 or more amino acids and do not include the amino acid motif HPQ (SEQ ID NO: 13). Another embodiment of the invention includes a peptide array comprising up to 2.9 million 5-mer peptides, representing the protein content encoded by the entire human genome, wherein the 5-mer peptides do not include any of the amino acids C and M, do not include amino acid repeats of 2 or more amino acids. It should be understood, that the sequences of the peptides at specific locations on the array is known.

According to further embodiments, each 5-mer peptide 308 comprising the population of up to 2.9 million peptides 310 of the array 300 may be synthesized with 5 cycles of wobble synthesis in each of the N-term of and C-term (see, for example, 306 and 306' FIG. 3). As used herein "wobble synthesis" refers to synthesis (through any of the means disclosed herein) of a sequence of peptides (either constant or random) which are positioned at the N-terminus or C-terminus of the 5-mer peptide 308 of interest. As illustrated in FIG. 3, the specific amino acids comprising the wobble synthesis at either the N- or C-terminal are represented by a "Z." According to various embodiments, wobble synthesis may include any number of peptides at the N-terminus or C-terminus, for example 1, 2, 3, 4, 5, 6, 7, 8, 9, 10 or more, even for example 15 or 20 peptides. Furthermore, wobble synthesis may comprise N-terminus and C-terminus having the same or differing number of wobble synthesized peptides.

According to various embodiments, the wobble oligopeptide compositions 306, 306' are flexible in terms of amino acid composition and in term of amino acid ratios/concentrations. For example, the wobble oligopeptide compositions may comprise a mixture of 2 or more amino-acids. An illustrative embodiment of such flexible wobble mix includes a wobble oligopeptide composition 306, 306' of glycine (G) and serine (S) at a ratio of 3:1. Other examples of a flexible wobble mixture include equal concentrations (e.g., equal ratios) of amino acids G, S, adenine (A), valine (V), aspartic acid (D), proline (P), glutamic acid (E), leucine (L), threonine (T) and/or equal concentrations (e.g., equal ratios) of amino acids L, A, D, lysine (K), T, glutamine (Q), P, F, V, tyrosine (Y). Other examples include the wobble oligopeptide compositions 306, 306' comprising any of the 20 known amino acids, in equal concentrations.

As disclosed herein, the wobble oligopeptide synthesis of the various embodiments allow for generating a peptide on an array having a combination of random and directed synthesis amino acids. For example, an oligopeptide probe on an array may comprise a combined 15mer peptide having a peptide sequence in the following format: ZZZZZ-5mer-ZZZZZ, where Z is an amino-acid from a particular wobble oligopeptide mixture.

In some embodiments, a feature may contain $10^7$ peptides. In some such embodiments, the population complexity for each feature may vary depending on the complexity of the wobble mixture. As disclosed herein, creating such complexity using wobble synthesis in a semi-directed synthesis enables the screening of binders on the array, using peptides with diversity up to $10^{12}$ per array. Examples of binder screen for Streptavidin and PSA are set forth below (additional protein targets, e.g., uPA or TNF are also possible according to the methods and systems set forth).

In practice, with reference to FIG. 3, an array 300 comprising a solid support 302 having a reactive surface 304 (e.g., a reactive amine layer for example) with a population of peptides 310 (such as a population of 5-mers representing the entire human proteome) immobilized thereto is provided. The exemplary 5-mer peptides comprising the population of peptides 310, according to such embodiment, does not include any of the amino acids C and M, does not include amino acid repeats of 2 or more amino acids and does not include the amino acid motif HPQ (SEQ ID NO: 13). According to such illustrative embodiment, such population of peptides 310 representing the entire human proteome would comprise 1,360,732 individual peptides comprising the population 310. In some embodiments, duplicates or repeats may be placed on the same array. For example, a population 310 comprising a single duplicate would comprise 2,721,464 individual peptides. Additionally, the population of peptides 310 each comprise an N-terminal and C-terminal wobble synthesis oligopeptide 306, 306', which for example consists of five amino acids each consisting of the amino acid glycine and serine in a 3:1 ratio, respectively.

Figure 4:
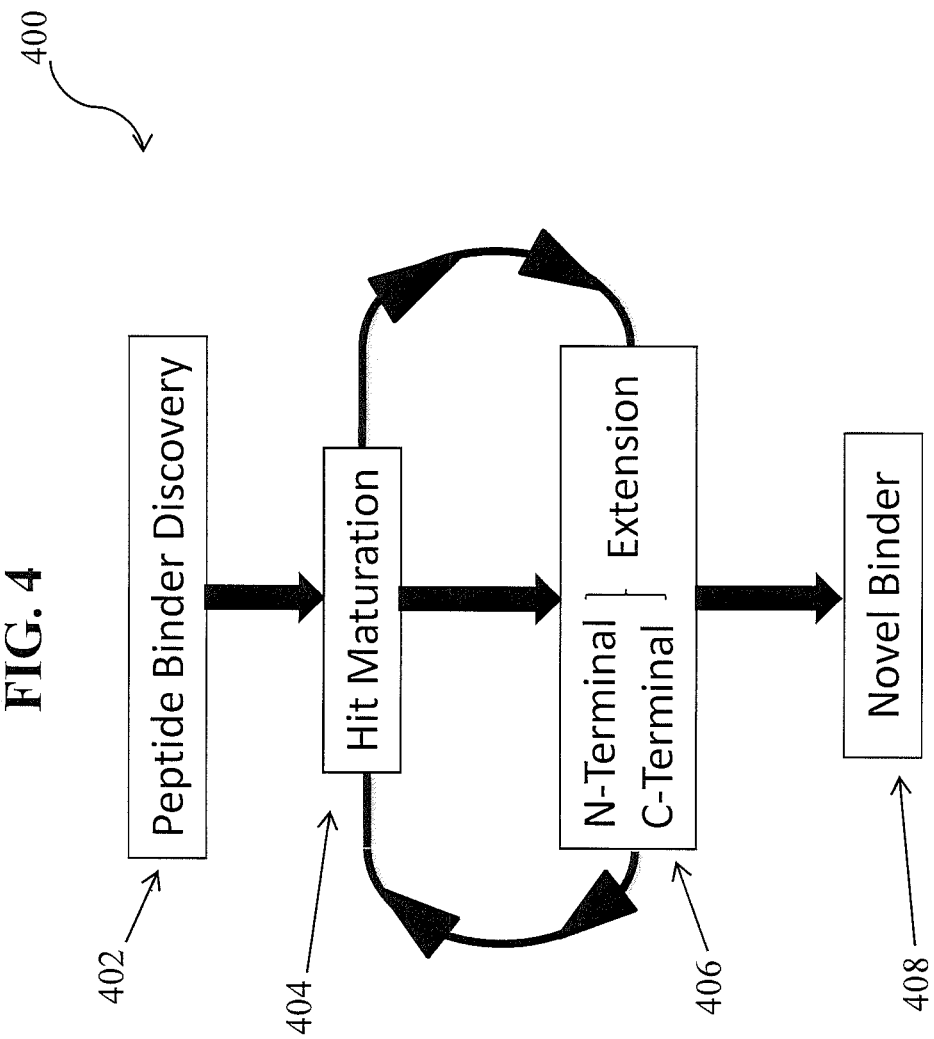
FIG. 4 is a schematic illustration of an embodiment of a process of the present disclosure.

Referring generally now to step 402 of process 400 of FIG. 4, in use an exemplary array 300 (FIG. 3) is exposed to a concentrated, purified protein of interest (as with standard microarray practice), whereby the protein may bind at any of the population of peptides 310, independent of the other peptides comprising the population 310. After exposure to the protein of interest, binding of the protein of interest to the peptide binders is assayed, for example, by way of exposing the complex of the individual peptide of the population 310 and protein to an antibody (specific for the protein) which has a reportable label (e.g., peroxidase) attached thereto. Because the peptide sequence of each 5-mer, at each location on the array, is known, it is possible to chart/quantify/compare/contrast the sequences (and binding strengths) of the binding of the protein to specific 5-mer peptide sequences. One such method of comparing the protein binding to the peptides comprising the population 310 is to review the binding in a principled analysis distribution-based clustering, such as described in, *Standardizing and Simplifying Analysis of Peptide Library Data*, Andrew D White et al, J Chem Inf Model, 2013, 53(2), pp 493-499, and illustrated herein. As is exemplified herein, the clustering of protein-5-mer binding (a.k.a., "hits") (shown in a principled analysis distribution-based clustering) indicates 5-mers having overlapping peptide sequences. As demonstrated in greater detail below, from the overlapping peptide sequences (of each cluster), a "core hit" peptide sequence (e.g., a peptide sequence shared by the prominent protein-peptide binding events of the array) can be identified, or at least hypothesized and constructed for further evaluation. (Note, it should be understood that an array, as exemplified herein, may identify more than one "core hit" peptide sequence. It should further be understood that it is possible for the "core hit" peptide sequence to comprise more amino acids than, for the example, the 5-mer peptide binders comprising the population of peptides due to possible identification of overlapping and adjacent sequences during principled analysis distribution-based clustering).

IV. Peptide Maturation:

Referring now to step 404 of process 400 graphically described in FIG. 4, upon identification of a core hit peptide sequence (through the process of peptide binder discovery 402 disclosed, described and exemplified herein), a process of "peptide maturation" 404 whereby the core hit peptide sequence is altered in various ways (through amino acid substitutions, deletions and insertions) at each position of the core hit peptide in order to further optimize/verify the proper core hit sequence. For example, according to some embodiments (for example, where the core hit peptide sequence comprises a given number, of, such as 7, amino acids), a maturation array is produced. According to the instant disclosure, the maturation array may have, immobilized thereto, a population of core hit peptides whereby each amino acid in the core hit peptide has undergone an amino acid substitution at each position.

In order to further describe the process of hit maturation 404, an example/hypothetical core hit peptide is described as consisting of a 5-mer peptide having the amino acid sequence $-M_1M_2M_3M_4M_5-$ (SEQ ID NO: 49). According to the instant disclosure, hit maturation 404 may involve any of, or a combination of any or all of, amino acid substitutions, deletions and insertions at positions 1, 2, 3, 4 and 5. For example, in regard to the hypothetical core hit peptide $-M_1M_2M_3M_4M_5-$ (SEQ ID NO: 49), embodiments of the instant disclosure may include the amino acid M at position 1 being substituted with each of the other 19 amino acids (e.g., $A_1M_2M_3M_4M_5-$ (SEQ ID NO: 50), $P_1M_2M_3M_4M_5-$ (SEQ ID NO: 51), $V_1M_2M_3M_4M_5-$ (SEQ ID NO: 52), $Q_1M_2M_3M_4M_5-$ (SEQ ID NO: 53), etc.). Each position (2, 3, 4 and 5) would also have the amino acid M substituted with each of the other 19 amino acids (for example, with position 2 the substitutions would resemble, $M_1A_2M_3M_4M_5-$ (SEQ ID NO: 54), $M_1Q_2M_3M_4M_5-$ (SEQ ID NO: 55), $M_1P_2M_3M_4M_5-$ (SEQ ID NO: 56), $M_1N_2M_3M_4M_5-$ (SEQ ID NO: 57), etc.). It should be understood that a peptide (immobilized on an array) is created comprising the substituted and/or deleted and/or inserted sequences of the core hit peptide.

In some embodiments of hit maturation 404 according to the instant disclosure, a double amino acid substitution may be performed. A double amino acid substation includes altering the amino acid at a given position (e.g., a M→P substitution, for example at position 1) and then substituting the amino acid at position 2 with each of the other 19 amino acids the amino acid at position 2. This process is repeated until all possible combinations of positions 1 and 2 are combined. By way of example, referring back to the hypothetical core hit peptide having a 5-mer peptide with amino acid sequence $-M_1M_2M_3M_4M_5-$ (SEQ ID NO: 49), a double amino acid substitution with regard to positions 1 and 2 may include, for example, a M→P substitution at position 1, and then a substation of all 20 amino acids at position 2 (e.g., $-P_1A_2M_3M_4M_5-$ (SEQ ID NO: 58), $-P_1F_2M_3M_4M_5-$ (SEQ ID NO: 59), $-P_1V_2M_3M_4M_5-$ (SEQ ID NO: 60), $-P_1E_2M_3M_4M_5-$(SEQ ID NO: 61), etc.), a M→V substitution at position 1, and then a substation of all 20 amino acids at position 2 (e.g., $-V_1A_2M_3M_4M_5-$ (SEQ ID NO: 62), $-V_1F_2M_3M_4M_5-$ (SEQ ID NO: 63), $-P_1V_2M_3M_4M_5-$ (SEQ ID NO: 60), $-V_1E_2M_3M_4M_5-$ (SEQ ID NO: 64), etc.), $M_4A$ substitution at position 1, and then a substation of all 20 amino acids at position 2 (e.g., $-A_1A_2M_3M_4M_5-$ (SEQ ID NO: 65), $-A_1F_2M_3M_4M_5-$ (SEQ ID NO: 66), $-A_1V_2M_3M_4M_5-$ (SEQ ID NO: 67), $-A_1E_2M_3M_4M_5-$ (SEQ ID NO: 68), etc.).

In some embodiments of hit maturation 404 according to the instant disclosure, an amino acid deletion for each amino acid position of the core hit peptide may be performed. An amino acid deletion includes preparing a peptide including the core hit peptide sequence, but deleting a single amino acid from the core hit peptide sequence (such that a peptide is creating in which the amino acid at each peptide is deleted). By way of example, referring back to the hypothetical core hit peptide having a 5-mer peptide with amino acid sequence $M_1M_2M_3M_4M_5$-(SEQ ID NO: 49), an amino acid deletion would include preparing a series of peptides having the following sequences -$M_2M_3M_4M_5$- (SEQ ID NO: 69); -$M_1M_3M_4M_5$- (SEQ ID NO: 69); -$M_1M_2M_4M_5$- (SEQ ID NO: 69); -$M_1M_2M_3M_5$- (SEQ ID NO: 69); and -$M_1M_2M_3M_4$- (SEQ ID NO: 69). It should be noted that, following an amino acid deletion of the hypothetical 5-mer, 5 new 4-mers are created. According to some embodiments of the instant disclosure an amino acid substitution or a double amino acid substation scan can be performed for each new 4-mer generated.

Similar to the amino acid deletion scan discussed above, some embodiments of hit maturation 404 disclosed herein may include an amino acid insertion scan, whereby each of the 20 amino acids is inserted before and after every position of the core hit peptide. By way of example, referring back to the hypothetical core hit peptide having a 5-mer peptide with amino acid sequence -$M_1M_2M_3M_4M_5$- (SEQ ID NO: 49), an amino acid insertion scan would include the following sequences, -$XM_1M_2M_3M_4M_5$- (SEQ ID NO: 70); -$M_1XM_2M_3M_4M_5$- (SEQ ID NO: 71); -$M_1M_2XM_3M_4M_5$- (SEQ ID NO: 72); -$M_1M_2M_3XM_4M_5$- (SEQ ID NO: 73); -$M_1M_2M_3M_4XM_5$- (SEQ ID NO: 74); and -$M_1M_2M_3M_4M_5X$- (SEQ ID NO: 75) (where X represents an individual amino, selected from the 20 known amino acids or a specific, defined subset of amino acids, whereby a peptide replicate will be created for each of the 20 or defined subset of amino acids).

It should also be understood that the amino acid-substituted peptides, double amino acid-substituted peptides, amino acid deletion scan peptides and amino acid insertion scan peptides described above may also include one, or both of, a N-terminal and C-terminal wobble amino acid sequence (similar to as described at 306, 306' of FIG. 3, for example). As with the N-terminal and C-terminal wobble amino acid sequences described in FIG. 3, the N-terminal and C-terminal wobble amino acid sequences may comprise as few as 1 amino acid or as many as 15 or 20 amino acids, and the N-terminal wobble amino acid sequence may be the same length as, longer than or shorter than the C-terminal wobble amino acid sequence. Further, the N-terminal and C-terminal wobble amino acid sequences may comprise any defined group of amino acids at any given ratios (for example, glycine and serine in a 3:1 ratio).

In a specific exemplified embodiment of hit maturation 404 described below, a core hit peptide of 7 amino acids (e.g., a 7-mer) undergoes exhaustive single and double amino acid screens, and includes both N-terminal and C-terminal wobble amino acid sequences which comprise three amino acids (all glycine).

Figure 11:
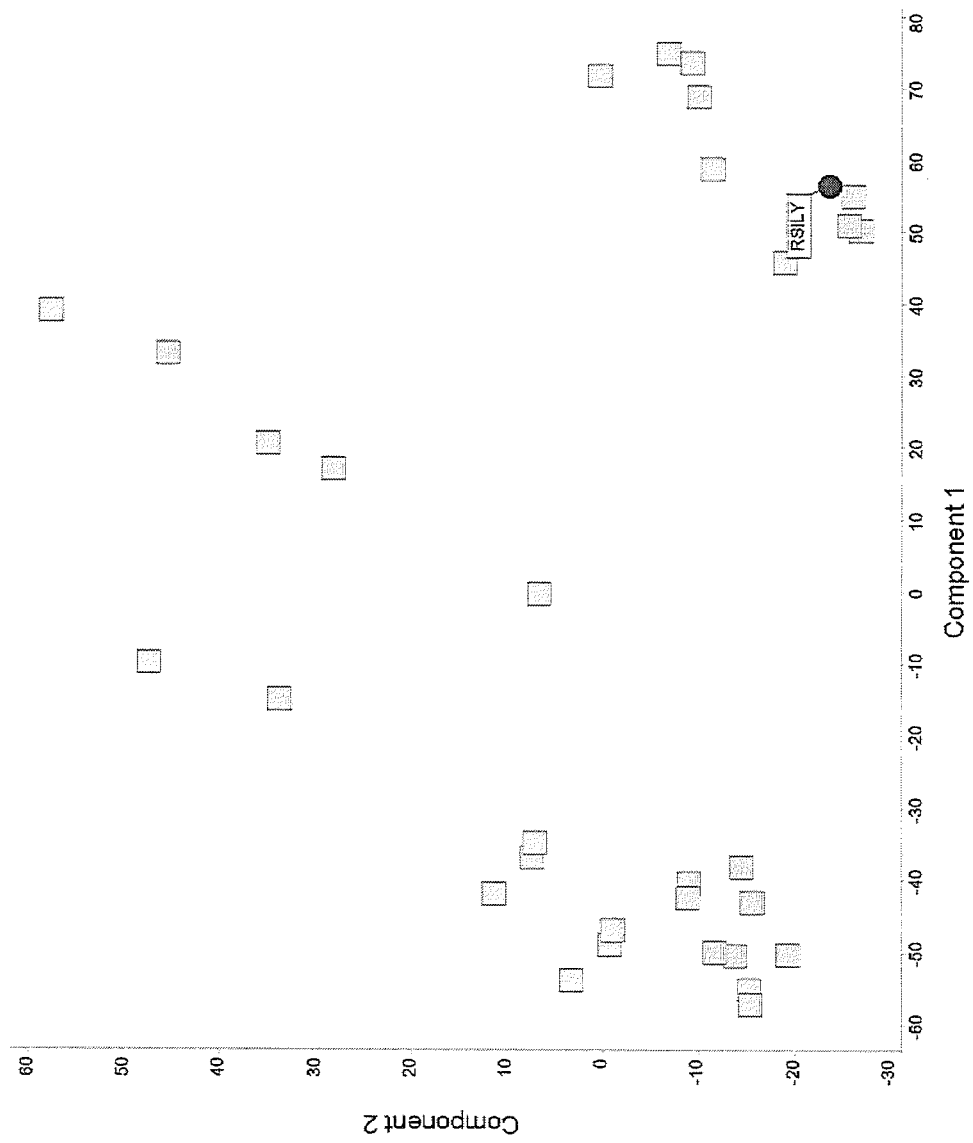
FIG. 11 is a PCA plot of consensus motifs (SEQ ID NO: 4) for the prostate specific antigen (PSA) binders generated through the three-step approach (Example 4).

Once the various substitution, deletion and insertion variations of the core hit peptide are prepared (for example, in immobilized fashion on a solid support such as a microarray), the strength of binding of the purified, concentrated target protein is assayed (FIG. 11). As shown in the Examples provided below, the process of hit maturation allows for refining the core hit peptide to an amino acid sequence demonstrating the most preferred amino acid sequence for binding the target protein with the highest affinity.

V. Peptide Extension (N-terminal and C-Terminal):

It is possible that motifs identified in 5-mer array experiments represent only short versions of optimal protein binders. We have developed a strategy of identifying longer motifs by extending sequences selected from 5-mer arrays experiments by one or more amino acids from one or both N- and C-terminus. Starting from a selected peptide and adding one or more amino acids on each terminus, one can create an extension library for further selection. For example, starting from a single peptide and using all 20 natural amino acids, one can create an extension library of 160,000 unique peptides. In some embodiments, each of the extended peptides is synthesized in replicates.

Referring now to step 406 of process 400 graphically described in FIG. 4, upon maturation of the core hit peptide (such that a more optimal amino acid sequence of the core hit peptide is identified for binding the target protein), the N-terminal and/or C-terminal positions undergo an extension step, whereby the length of the matured core hit peptide 512 is further extended for increasing the specificity and affinity for the target peptide.

Figure 5:
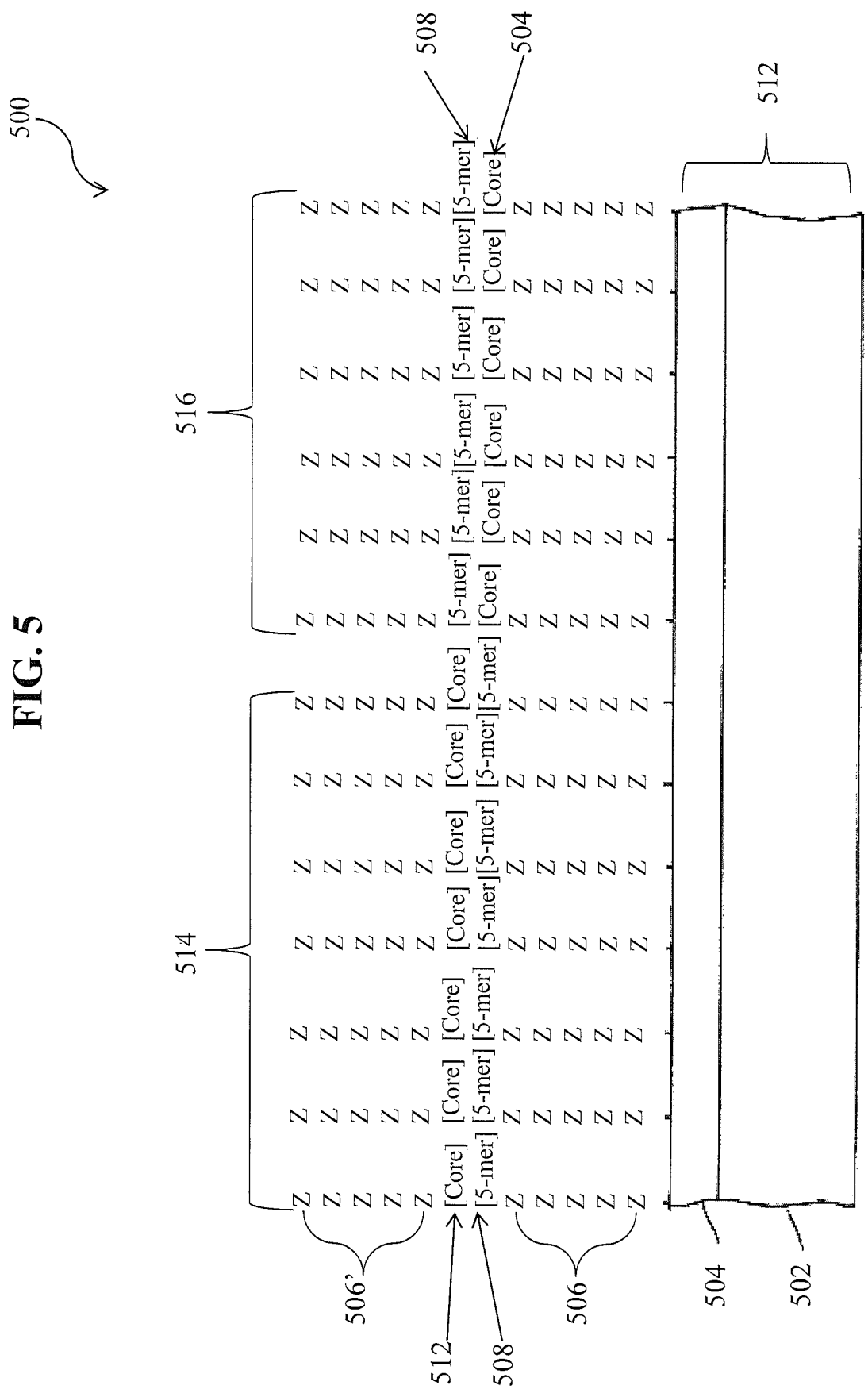
FIG. 5 is a schematic view illustrating another embodiment of an array comprising peptide probes thereon in accordance with the present disclosure.

According to various embodiments of N-terminal extension of the instant disclosure, and with reference to FIG. 5, once the matured core hit peptide sequence 512 is identified through the maturation process (404 of FIG. 4), each specific peptide probe of-the population (represented as a population of 5-mers, 308 of FIG. 3) from the peptide binder discovery step (302, FIG. 3), is added (or synthesized onto) the N-terminal end of a matured core hit peptide 512. In this manner, the most C-terminus amino acid of each peptide sequence 308 (of the population), exemplified as a population of 5-mers in FIG. 3, is added (or synthesized) directly adjacent to the most N-terminus amino acid of the matured core hit peptide 512.

Likewise, according to various embodiments of C-terminal extension of the instant disclosure, and with reference to FIG. 5, once the matured core hit peptide sequence 512 is identified through the maturation process (404 of FIG. 4), each specific peptide probe of the population (represented as a population of 5-mers, 308 of FIG. 3) from the peptide binder discovery step (302, FIG. 3), is added (or synthesized) onto) the C-terminal end of a matured core hit peptide 512. In this manner, the most N-terminus amino acid of each peptide sequence 308, exemplified as a population of 5-mers in FIG. 3, is added (or synthesized) directly adjacent to the most C-terminus amino acid of the matured core hit peptide 512.

According to some embodiments of the instant disclosure (FIG. 5) one of, or both of, the matured core hit peptides used in C-terminal extension and N-terminal extension may also include one, or both of, a N-terminal and C-terminal wobble amino acid sequence (similar to as described at 306, 306' of FIG. 3). As with the N-terminal and C-terminal wobble amino acid sequences described in FIG. 3, the N-terminal and C-terminal wobble amino acid sequences may comprise as few as 1 amino acid or as many as 15 or 20 amino acids (or more), and the N-terminal wobble amino acid sequence may be the same length as, longer than, or shorter than the C-terminal wobble amino acid sequence. Further, the N-terminal and C-terminal wobble amino acid sequences may comprise any defined group of amino acids at any given ratios (for example, glycine and serine in a 3:1 ratio).

By way of example, on FIG. 5, a peptide extension array 500 is shown, having a population of peptides for N-terminal extension 514 and a population of peptides for C-terminal extension 516. Each population of peptides 514, 516 may contain the full population of peptides 310 from peptide array 300 (used in the step of peptide binder discovery 404). As further illustrated, each peptide of both populations of peptides 514, 516 may contain the same matured core peptide 512, each with a different peptide probe 508 (of the population of probes from the peptide binder discovery step 302, FIG. 3). Also shown in FIG. 5, each peptide of the populations 514, 516 includes N-terminal and C-terminal wobble amino acid sequences.

In use, an extension array 500 (including populations 514 and 516) is exposed to a concentrated, purified protein of interest (as in peptide binder discovery, step 401 of process 400), whereby the protein may bind at any peptide of either population 514, 516, independent of the other peptides comprising the populations 514, 516. After exposure to the protein of interest, binding of the protein of interest to the peptide of the populations 514, 516 is assayed, for example, by way of exposing the complex of the individual peptide of the populations 514, 516 and protein to an antibody (specific for the protein) which has a reportable label (e.g., peroxidase) attached thereto (it should also be understood the protein of interest may be directly labelled with a reporter molecule). Because the peptide probe sequence 508 (of each 5-mer) for each location on the array, is known, it is possible to chart/quantify/compare/contrast the sequences (and binding strengths) of the binding of the protein to the specific probe comprising the matured core hit peptide 512 with the respective peptide probe 508. An exemplary method of comparing the protein (of interest) binding to the matured core hit peptide 512—peptide probe 508 combination (comprising either population 514 or 516) is to review the binding strength in a principled analysis distribution-based clustering, such as described in, *Standardizing and Simplifying Analysis of Peptide Library Data*, Andrew D White et al, J Chem Inf Model, 2013, 53(2), pp 493-499, and illustrated herein (for example at Graphs 3 and 4. As is exemplified herein, clustering of protein binding to the respective probes (of populations 514, 516) shown in a principled analysis distribution-based clustering indicates peptide probe 5-mers 508 having overlapping peptide sequences. As demonstrated in greater detail below, from the overlapping peptide sequences (of each cluster), an extended, matured core hit peptide sequence can be identified, or at least hypothesized and constructed for further evaluation. In some embodiments of the instant application, an extended, matured core hit peptide undergoes a maturation process (as described and exemplified herein and illustrated at step 404 of FIG. 4).

The N-terminal and C-terminal extension processes disclosed herein demonstrate surprising and unexpected results. The N-terminal and C-terminal extension processes do not simply demonstrate a "repeat" of the core hit peptide sequence (from the peptide binder discovery step 402), but instead show specific and uniform N- and C-terminal amino acid junction sequences, which contribute to increasing the length, specificity and affinity of the matured core hit for the protein of interest. Without being bound by a particular theory, the inventors suggest that the surprising and unexpected results of the N- and C-terminal extension processes, step 406, may be due to highly specific amino acid interactions at the junction of the matured core hit peptide 512 and the peptide binder 508.

Additional rounds of optimization of extended peptide binders are also possible. For example, a third round of binder optimization may include extension of the sequences identified in the extension array experiments with glycine (G) amino acid. Other optimization may include creating double substitution/deletion libraries that include all possible single and double substitution/deletion variants of the reference sequence, i.e., the peptide binder optimized and selected in any of the previous steps.

VI. Specificity Analysis of Extended, Matured, Core Hit Peptide Binders:

Following identification of an extended, matured core hit peptide a specificity analysis may be performed by any method of measuring peptide affinity and specificity available in the art. One example of a specificity analysis includes a "Biacore™" system analysis which is used for characterizing molecules in terms of the molecules interaction specify to a target, the kinetic rates (of "on," binding, and "off," disassociation) and affinity (binding strength). Biacore™ is a trademark of General Electric Company and is available via the company website.

Figure 6:
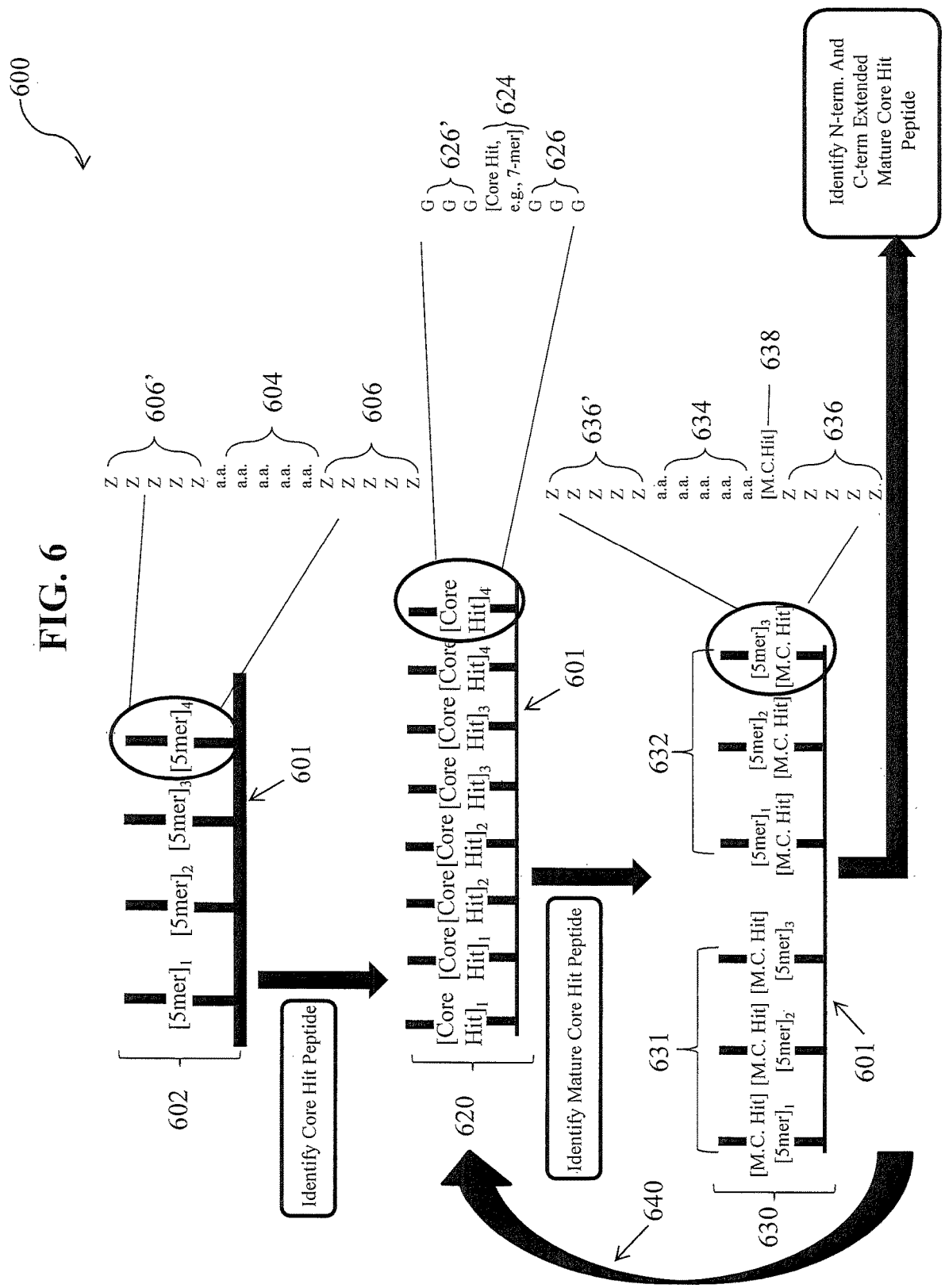
FIG. 6 is a schematic view depicting an embodiment of the process of FIG. 4.

FIG. 6 is a brief schematic overview of the method of novel peptide binder identification (e.g., process 400 of FIG. 4). As shown, the peptide binder discovery 602 is performed by preparing (e.g., through maskless array synthesis) a population of peptides on an array 601. As illustrated, each peptide includes 5 "cycles" of N-terminal wobble synthesis 606' and C-terminal wobble synthesis 606 (e.g., both N- and C-terminal wobble synthesis comprises five amino acids). It should be understood that the wobble synthesis of the C- and N-terminal may comprise any composition as noted above (for example, only amino acids G and S, in a 3:1 [G:S] ratio). Each peptide is also shown as comprising a 5-mer peptide binder 604, which as noted above may comprise up to 2.9 million different peptide sequences such that an entire human proteome is represented. Further, it should be noted that the different peptide binders 604 may be synthesized according to specific "rules" (for example, no C or M amino acids, no repeats of the same amino acid in consecutive order, and no HPQ (SEQ ID NO: 13) amino acid motifs). As described above, a protein target of interest (for example, in purified and concentrated form) is exposed to the peptide binders 604, and binding is scored (e.g., by way of a principled clustering analysis), whereby a "core hit peptide" sequence is identified based on overlapping binding motifs.

Upon identification of a core hit peptide sequence, an exhaustive maturation process 620 may be undertaken. In some embodiments, the core hit peptide (exemplified as a 7-mer, 624) is synthesized on an array 601 with both N- and C-terminal wobble (shown at step 620 as 3 cycles of N- and C-terminal wobble of only G amino acid, although the wobble amino acid may vary as noted above). In some embodiments of exhaustive maturation, a peptide is synthesized on the array 601 wherein every amino acid position of the core hit peptide 624 is substituted with each of the other 19 amino acids or a double amino acid substitution (as described above) is synthesized on the array 601 or an amino acid deletion scan is synthesized on the array 601, or an amino acid insertion scan is synthesized on the array 601. In some cases, all of the above maturation processes are performed (and the repeated as described above for the new peptides generated as a result of the amino acid deletion and insertion scans). Upon synthesis of the maturation array 620 comprising the various peptides (inclusive of the substitutions, deletions and insertions described herein), the target protein is exposed to the modified core hit peptides 624 synthesized on the maturation array 620, and strength of binding is assayed, whereby a "matured core hit peptide" sequence is identified.

After identification of a "matured core hit peptide" sequence, one of, or both of N- and C-terminal extension may be performed (shown at 630 as including both N-terminal extension 632 and C-terminal extension 631). N-terminal and C-terminal extension involve the synthesis of matured core hit peptide having the population of (e.g., 5-mer) peptide binders 604 synthesized at the N-terminal or C-terminal respectively. As shown at 631, C-terminal extension involves five rounds of wobble synthesis (as described above) 636 and the population of 5-mer peptide binders 634 being synthesized C-terminally of the matured core hit peptide 638, then another 5 cycles of wobble synthesis 636' N-terminally. Similarly, as shown at 632, N-terminal extension involves five rounds of wobble synthesis (as described above) 636 being synthesized C-terminally of the matured core hit peptide 638, then the population of 5-mer peptide binders 634 and another 5 cycles of wobble synthesis 636' synthesized N-terminally (of the matured core hit peptide 638). Upon synthesis of the extension array 630 comprising the various extension peptides (inclusive of C-terminal and N-terminal extension peptides), the target protein is exposed to the C-terminal and N-terminal extension peptide populations 631, 632 synthesized on the extension array 630, and binding is scored (e.g., by way of a principled clustering analysis), whereby a C-terminally, N-terminal extended, matured core hit peptide sequence is identified. As represented by arrow 640, according to some embodiments, after the extended, matured core hit peptide is identified, the maturation process 620 for the extended matured core hit peptide may be repeated (in any way as described above), and then the extension process repeated for any altered peptide sequence resulting therefrom.

VII. Prostate-Specific Antigen (PSA) Binder Peptides

The peptide binders specific for PSA are listed below (and also in Table 2).

| SEQ ID NO: | |
|---|---|
| 1 | FEVYL |
| 2 | WTVYA |
| 3 | WEVHL |
| 4 | RSILY |
| 5 | NGFEVYLPG |
| 6 | SEWTVYAGN |
| 7 | TGWEVHLGK |
| 8 | SCRSILYGQ |
| 9 | GTGFEVYIPGA |
| 10 | ASEWTVYAGNK |
| 11 | GTGWEVHLGKG |
| 12 | QSCRSILYGDG |

It should be understood that these novel peptide binders specific for PSA can be used in any number of diagnostic assays, including but not limited to microarray, immunohistochemistry, chromatography, enzyme-linked immunosorbent assay (ELISA), in situ-hybridization, and assays incorporating one or more nucleotides linked to the novel peptide binders. As such, the novel peptide binders disclosed herein may be used in diagnosing prostate cancer in patients.

Furthermore, each novel peptide binder disclosed herein may be combined with one or more additional peptide binders, for example, to form a panel of peptide binders (e.g., as in a multiplexed diagnostic assay). Such panel may aid in diagnosing prostate cancer or discriminating between prostate cancer and benign hyperplasia.

In some embodiments, the invention is a method of diagnostically evaluating a subject for prostate cancer by obtaining a test sample and assaying the sample for PSA with one or more of the novel peptide binders disclosed herein. In some embodiments, PSA within the test sample of the subject is quantified for determining the presence of prostate cancer. Test samples include body fluids, for example, blood, plasma, serum, urine, prostate tissue and prostate fluid (i.e., fluid immediately surrounding the prostate gland). Test samples further include solid tissue or organ samples obtained e.g., by biopsy. Separated cells may be obtained from the body fluids or the tissues or organs by separating techniques such as centrifugation or cell sorting. The sample may be frozen, fresh, fixed (e.g. formalin fixed) or embedded (e.g. paraffin embedded). The sample can be subjected to a variety of well-known post-collection preparative and storage techniques prior to assessing the amount of the marker in the sample.

The use of peptide binders may be combined with assaying mRNA or DNA from a genetic biomarker of interest using hybridization, polymerase chain reaction (PCR) analysis, RNase protection assay, or using array hybridization, e.g., with DNA SNP chip microarrays, which are commercially available, including DNA microarray snapshots. Additional biomarkers may be detected by measuring a physical or chemical property specific for the polypeptide such as its precise molecular mass or NMR spectrum, using e.g., biosensors, optical devices coupled to immunoassays, biochips, analytical devices such as mass-spectrometers, NMR-analyzers, or chromatography devices, microplate ELISA readers, fully-automated or robotic immunoassays (e.g., ECLE-SYS™ analyzers), Cobalt Binding Assay and latex agglutination assays (available for example on Roche-Hitachi analyzers).

For the detection of PSA with the novel peptide binders disclosed herein a wide range of immunoassay techniques are available, see, e.g., U.S. Pat. Nos. 4,016,043, 4,424,279, and 4,018,653. These include both single-site and two-site or "sandwich" assays of the non-competitive types, as well as in the traditional competitive binding assays. Some such assays may also include direct binding of a labelled antibody to a target biomarker. The binding may be detected by measuring electro-chemiluminescence (see Richter, M. M., Chem. Rev. 104 (2004) 3003-3036), magnetic resonance (NMR) spectroscopy, gas chromatography-mass spectrometry (GC-MS), liquid chromatography-mass spectrometry (LC-MS) and various forms of HPLC.

As used herein, a subject includes any human subject experiencing signs, symptoms, or other indicators of prostate pathology or a subject for whom prostate cancer screening is recommended.

In one embodiment, the present invention is a method for diagnosing prostate cancer in a subject by determining the presence or amount of PSA in a test sample from the subject. Some embodiments comprise providing a diagnosis of prostate cancer if the amount of PSA in the sample is greater than a reference concentration.

According to other embodiments of the instant disclosure, a method of treating prostate cancer, or preventing or delaying the onset or of prostate cancer, in the subject is provided. Some such embodiments comprise administering a compound, comprising a peptide binder disclosed herein, which can bind and alter the function of PSA. The peptide binder(s) of such compound may include one of more peptide binders comprising the amino, acid sequence selected from the group consisting of SEQ ID NO. 1-12, or having at least 80% sequence homology with one of SEQ ID NO. 1-12.

In some embodiments, the instant disclosure relates to the use of the novel peptide binders for the manufacture of a medication for the treatment or prophylaxis of prostate cancer.

In other embodiments, the instant disclosure relates to a method of determining the likelihood of an agent having a therapeutic effect in the treatment of prostate cancer, comprising using one more novel peptide binders disclosed herein for detecting or quantifying the amount of PSA in a subject test sample before and after exposing a test subject to said agent.

In some embodiments, the instant disclosure provides a kit comprising one or more novel peptide binders disclosed herein. Such kit may comprise a peptide binder(s) comprising the amino acid sequence selected from the group consisting of SEQ ID NO. 1-12, or having at least 80% sequence homology with one of SEQ ID NO. 1-12, and optionally, additional peptide binders.

VIII. Streptavidin Binder Peptides

The peptide binders specific for streptavidin are listed below (and also in Table 1).

| SEQ ID NO: | |
|---|---|
| 13 | HPQ |
| 14 | LAEYH |
| 15 | RPGWK |
| 16 | PAWAH |
| 17 | FDEWL |
| 18 | WTHPQFE |
| 19 | DYLAEYHGG |
| 20 | YERPGWKLS |
| 21 | PAPAWAHGG |
| 22 | NSFDEWLQK |
| 23 | WTHPQFEQK |
| 24 | ADYLAEYHGG |
| 25 | YERPGWKLGT |
| 26 | DPAPAWAHGG |
| 27 | NSFDDWLAKGG |

These novel peptide binders specific for streptavidin can be used in any application where detection or capture of streptavidin, a tag representing a fragment of streptavidin, or a streptavidin-biotin complex is required. The assays include microarray, immunohistochemistry, chromatography; enzyme-linked immunosorbent assay (ELISA), in situ-hybridization, and assays incorporating one or more nucleotides linked to the novel peptide binders.

For example, the streptavidin binding peptides of the present invention can be used for affinity capture of target molecules comprising the Strep-tag II sequence, see David S Wilson et al, (2001) *The use of mRNA display to select high-affinity protein-binding peptides* PNAS vol. 98, no. 7, 3750-3755.

In some embodiments, the instant disclosure provides a kit comprising one or more novel peptide binders specific for streptavidin disclosed herein. Such kit may comprise a peptide binder(s) comprising the amino acid sequence selected from the group consisting of SEQ ID NO. 13-27, or having at least 80% sequence homology with one of SEQ ID NO. 13-27, and optionally, additional peptide binders.

EXAMPLES

Example 1. Streptavidin Binder Discovery Using Comprehensive 5-Mer Peptide Arrays Array Design and Synthesis: An array having 2,476,099 peptides (representing a comprehensive list of all possible 5-mer peptides, excluding cysteine) was designed. We also designed a smaller array of 5-mer peptides by using all combinations of 18 natural amino acids excluding cysteine and methionine, any dimer or a longer repeat of the same amino acid, as well as any peptide containing HR, RH, HK, KH, RK, KR, HP, and PQ sequences to create a library of 1,360,732 unique peptides. This library had an advantage of using two replicates of each peptide on the same array to increase the confidence of the conclusions drawn from array data.

Each 5-mer peptide is synthesized with 5 cycles of wobble synthesis in the N-term and C-term. The wobble mixture compositions can be a mix of 2 or more amino-acids, for example a flexible wobble mix may include: a G:S mixture (in a 3:1 ratio), equal quantities of GAVDPSELT (SEQ ID NO: 28) or equal quantities of LADKTQPFVY (SEQ ID NO: 29). The wobble synthesis in effect allows a combination of random and directed synthesis yielding a combined 15-mer peptide. The peptide sequence would be in the following format: ZZZZZ-5mer-ZZZZZ, where Z is an amino-acid from a particular wobble mixture. Since each peptide synthesis feature contains up to $10^7$ peptides, the population of each peptide per feature will vary and would be proportional to the complexity of the wobble mixture. Creating such complexity using wobble synthesis in a semi-directed synthesis allows for screening of binders on the array, using peptides with diversity up to $10^{12}$ per array.

Binding Assay: Streptavidin labelled with Cy5 was incubated at 25° C. for 1 hr in 1×TE binding buffer with 1% alkali soluble casein. Array was washed 3× with 1×TE buffer and finally with 0.1×TE buffer and scanned using a 2 micrometer scanner.

Image Processing:' Image analysis and signal extraction were performed using NimbleGen DEVA software. For the library of 2,476,099 5-mer peptides, data were collected and averaged from three array slides and for the library of 1,360,732 5-mer peptides two slides were used for data analysis.

Figure 7:
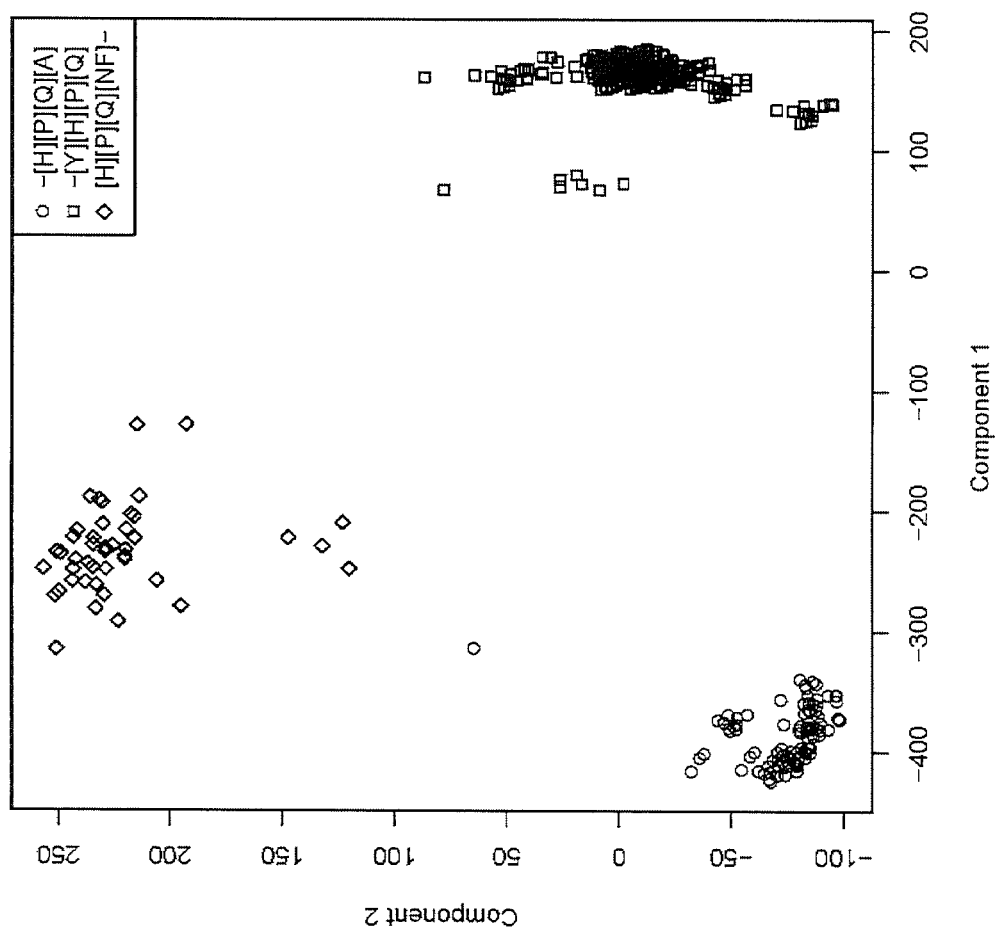
FIG. 7 is a PCA plot of consensus motifs (SEQ ID NOS 30-31 and 76, respectively, in order of appearance) for a streptavidin (SA) binder (Example 1).

Data analysis and Results: 424 sequences with the highest average intensity and coefficient of variation (CV) values less than 15% were selected from 2,476,099 peptide arrays. The sequences were clustered based on distances using the standard BLOSUM 62 substitution matrix as implemented by an R package 'PEPLIB' (see, Standardizing and Simplifying Analysis of Peptide Library Data, Andrew D White et al, J Chem Inf Model, 2013, 53(2), pp 493-499). The distances of the 5-mer peptides are plotted on the first two components of a PCA plot. Consensus motifs for each cluster are reported in FIG. 7. The three dense clusters indicate streptavidin binders with sequences HPQA (SEQ ID NO: 30), YHPQ (SEQ ID NO: 31) and HPQ[NF] (SEQ ID NO: 76). The results are consistent with previously published findings that utilized mRNA display for discovery of streptavidin binders (see David S Wilson et al, (2001) *The use of mRNA display to select high-affinity protein-binding peptides* PNAS vol. 98, no. 7, 3750-3755.

Figure 8:
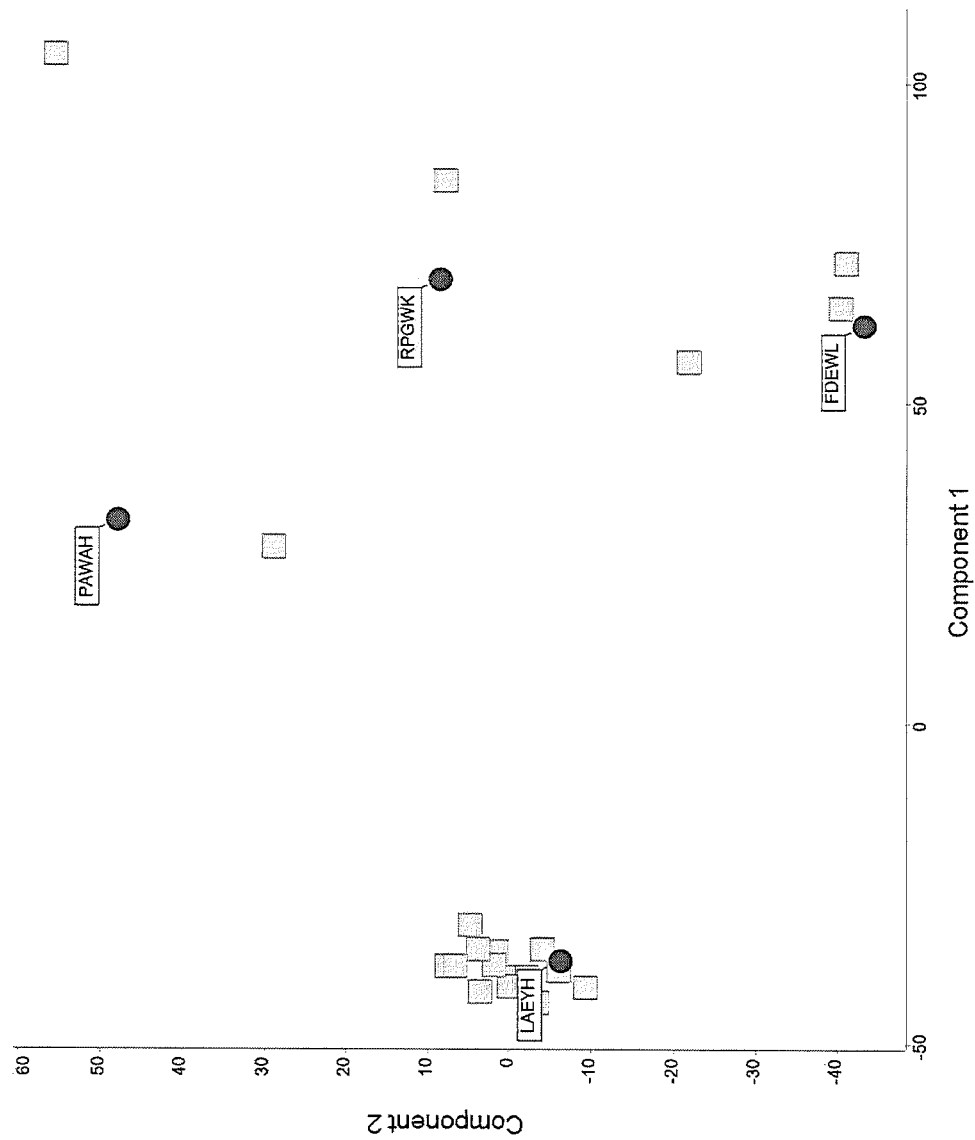
FIG. 8 is a PEPLIB analysis of consensus motifs (SEQ ID NOS 14, 16, 17 and 15, respectively, in order from left to right) for a streptavidin (SA) binder (Example 1).

To identify potential secondary streptavidin binders, 24 sequences with the highest average intensity were selected from 1,360,732 peptide arrays that by design did not include peptides with the dominant HPQ motif (SEQ ID NO: 13). The sequences were clustered based on distances using the R package 'PEPLIB' as shown in (FIG. 8). From this analysis four potential secondary streptavidin binders, LAEYH (SEQ ID NO: 14), RPGWK (SEQ ID NO: 15), PAWAH (SEQ ID NO: 16), and FDEWL (SEQ ID NO: 17), were selected for the next round of binder optimization.

Example 2. Streptavidin Binder Optimization Using Extension Peptide Arrays

Array Design: It is possible that motifs identified in 5-mer array experiments represent only short versions of optimal streptavidin binders. We have developed a strategy of identifying longer motifs by extending sequences selected from 5-mer arrays experiments by two amino acids from both N- and C-terminus using all 20 natural amino acids shown by X in Table 1. Each of the extension libraries includes 160,000 unique peptides synthesized in five replicates. Streptavidin binding assay and image processing was performed as described in Example 1.

TABLE 1

| Sequences selected from 5-mer libraries | SEQ ID NO: | Extension libraries | SEQ ID NO: | Sequences selected from extension libraries | SEQ ID NO: |
|---|---|---|---|---|---|
| HPQ | 13 | XXHPQXX | | WTHPQFE | 18 |
| LAEYH | 14 | XXLAEYHXX | 37 | DYLAEYHGG | 19 |
| RPGWK | 15 | XXRPGWKXX | 38 | YERPGWKLS | 20 |
| PAWAH | 16 | XXPAWAHXX | 39 | PAPAWAHGG | 21 |
| FDEWL | 17 | XXFDEWLXX | 40 | NSFDEWLQK | 22 |

| Double substitution/deletion libraries | SEQ ID NO: | Sequences selected from substitution/deletion libraries | SEQ ID NO: |
|---|---|---|---|
| GGWTHPQFEGG | 32 | WTHPQFEQK | 23 |
| GGDYLAEYHGG | 33 | ADYLAEYHGG | 24 |
| GYERPGWKLSG | 34 | YERPGWKLGT | 25 |
| GGPAPAWAHGG | 35 | DPAPAWAHGG | 26 |
| GNSFDEWLQKG | 36 | NSFDDWLAKGG | 27 |

Data analysis and Results: Sequences with the highest average intensity were selected for further analysis. Top sequences from each library are listed in Table 1.

Example 3. Streptavidin Binder Optimization Using Double Substitution/Deletion Peptide Arrays Array Design: The third round of binder optimization included extension of the sequences identified in the extension array experiments with glycine (G) amino acid to make them 11-mer peptides as shown in Table 1 followed by design of double substitution/deletion libraries that include all possible single- and double substitution/deletion variants of the reference sequence. Streptavidin binding assay and image processing for substitution/deletion arrays was performed as described in Example 1.

Data analysis and Results: The data are first analyzed by a single substitution plot which is similar to the standard alanine scan but includes substitutions of all 20 amino acids followed by binder optimization using double substitution analysis. An example of this analysis is shown in FIG. 9 for GGPAPAWAHGG sequence (SEQ ID NO: 35).

Figure 9:
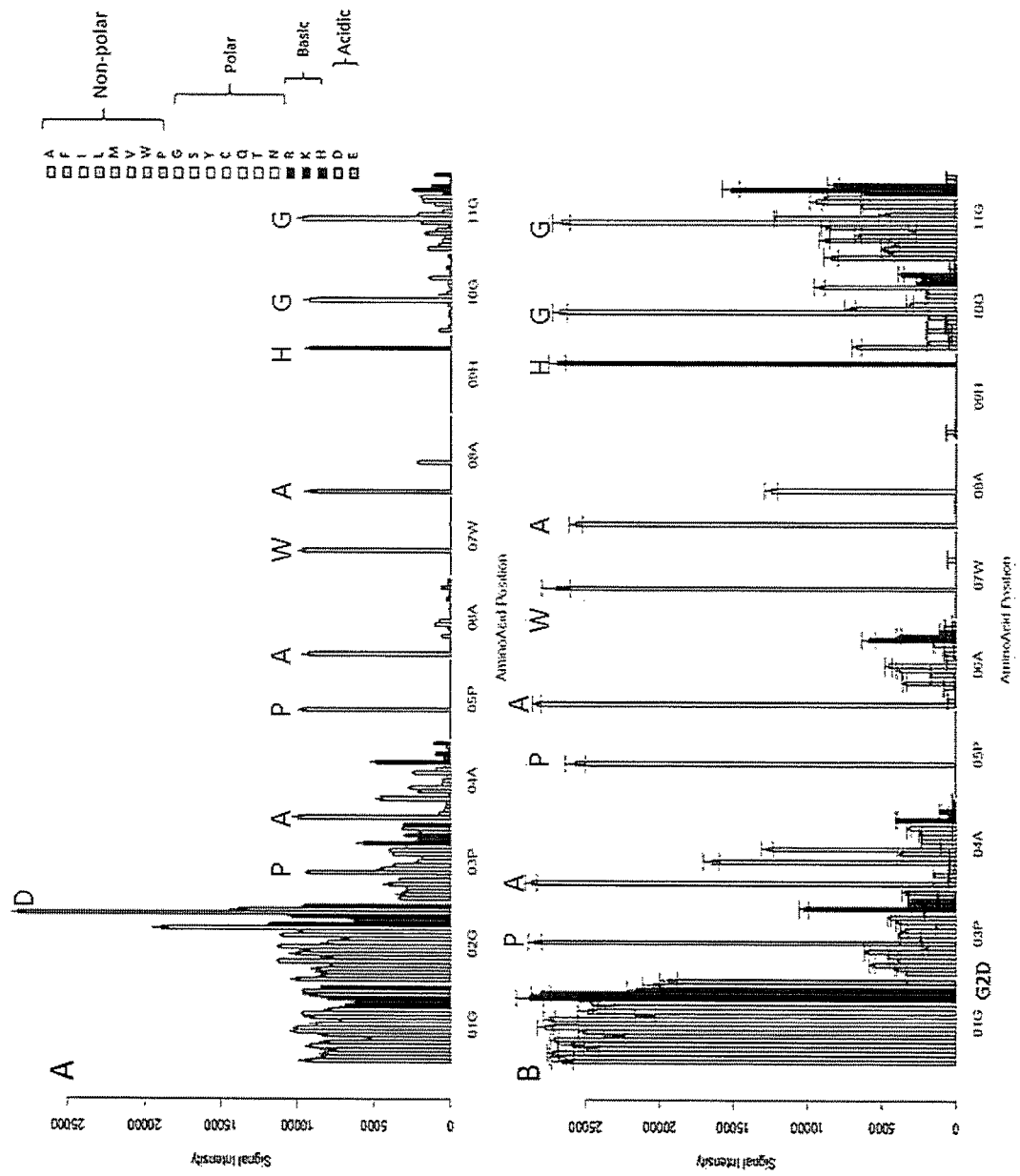
FIG. 9 is a PCA plot of consensus motifs for an optimized streptavidin (SA) binder (Examples 2-3). A discloses SEQ ID NO: 26 and B discloses SEQ ID NO: 21

FIG. 9, panel A shows that PAWAH motif (SEQ ID NO: 16) originally selected from the 5-mer array and its extended PAPAWAHGG (SEQ ID NO: 21) version represent the most specific amino acids at positions 3-11. The amino acid scan at position 2 suggests that G to D substitution would have a dramatic increase in the binding signal. The advantage of double substitutions included in the library is demonstrated by FIG. 9, panel B, which shows a substitution plot for peptides that have D at position 2. Indeed, substitution of D for G at position 2 increased signal intensity almost 3-fold without changing specificity of other amino acid in the motif. Top sequences selected by double substitution analysis for all five streptavidin motifs are shown in Table 1.

Example 4. Prostate Specific Antigen (PSA) Binder Discovery and Optimization Using Systematic Three Step Approach To test Systematic Binder Discovery Approach that consists of sequential application of three peptide arrays: 1) 5-mer Array, 2) Extension Array, and 3) Double Substitution/Deletion Array we chose as a target human prostate specific antigen (PSA).

Array Design: 5-mer array was designed by using all combinations of 18 natural amino acids excluding cysteine and methionine, any dimer or a longer repeat of the same amino acid, as well as any peptide containing HR, RH, HK, KH, RK, KR, HP, and PQ sequences to create a library of 1,360,732 unique peptides. Extension Arrays were designed by extending sequences selected from 5-mer arrays experiments by two amino acids from both N- and C-terminus using all 20 natural amino acids. Double Substitution/Deletion Arrays were designed by extension of sequences identified in the extension array experiments with glycine (G) amino acid to make them 11-mer peptides and creating a library that includes all possible single- and double substitution/deletion variants of the original sequence.

Array Synthesis: 5-mer Arrays were synthesized with 5 cycles of synthesis using a mixture of G and S amino acids in a 3:1 ratio, respectively at the N- and C-terminus of each of the 5-mer peptide. Extension and Double Substitution/Deletion Arrays were synthesized directly without using flanking wobble synthesis.

Binding Assay: PSA labelled with biotin using EZ-Link NHS-PEG4-biotinylation kit (Thermo Fisher Sci., Inc. Rockford, Ill.) was incubated in SecureSeal hybridization chamber (Grace Bio-Labs, Bend, Ore.) at concentration 100 ng/ml in 1×TE binding buffer with 1% alkali soluble casein at 25° C. for 12 hrs. Array was washed 3× with 1×TE buffer and stained with Streptavidin Cy5 in 1× binding buffer with 1% alkali soluble casein at 25° C. for 1 hr, and washed 3× with 1×TE buffer and finally with 0.1×TE buffer and scanned using a 2 micrometer MS200 scanner (Roche/Nimblegen, Madison, Wis.).

Data analysis: Image analysis and signal extraction performed using NimbleGen DEVA software, and peptides with fluorescent signal are identified. The 5-mer sequences for the binding peptides are identified and clustered based on distances using the standard BLOSUM 62 substitution matrix as implemented by an R package 'PEPLIB' (see, White et al., 2013, cited above). The distances of the 5-mer peptides are plotted on the first two components of a PCA plot. Consensus motifs for each cluster are reported in the graph.

Figure 10:
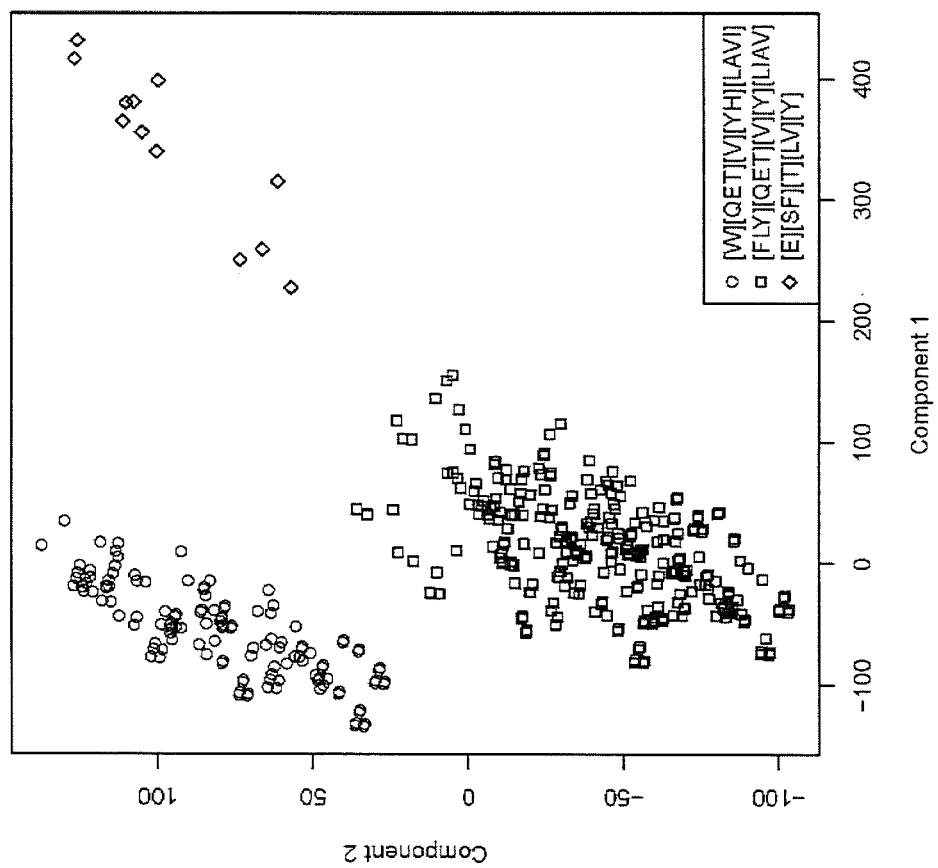
FIG. 10 shows binding affinities of prostate specific antigen (PSA) binder peptides (SEQ ID NOS 78-79 and 82, respectively, in order of appearance) generated through a three-step approach (Example 4).

Results: From 5-mer Array experiments, 405 sequences with the highest average signal intensity were identified. The data is shown in FIG. 10. Two major clusters, W[QET]V[YH][LAVI] (SEQ ID NO: 78) and [FLY][QET]VY[LIAV] (SEQ ID NO: 79), showed very similar motifs and included majority, 393, of the 405 sequences. For further analysis, we selected three sequences from these clusters, FEVYL (SEQ ID NO: 1), WTVYA (SEQ ID NO: 2) and WEVHL (SEQ ID NO: 3), ranked 1, 3 and 28 by their binding signal to PSA, respectively. The reason behind this was to choose mostly diverse sequences from the clusters and follow their evolution and binding properties in the next array designs.

Two dominant F[QET]VY[LI] (SEQ ID NO: 80) and W[QET]V[YH][LAV] (SEQ ID NO: 81) clusters described above were related by having similar amino acids F or W at position 1 and V at position 3. To find other possible binder motifs we excluded sequences with these features from the 5-mer Array data and performed PEPLIB analysis with top 32 sequences from the remaining dataset as shown in FIG. 11. One of the clusters, RS[KI]LY (SEQ ID NO: 41), was significantly distant from two dominant clusters identified in the original dataset. Sequence RSILY (SEQ ID NO: 4) ranked 307 in the original list of 405 sequences was selected for the next steps of binder optimization.

Figure 12:
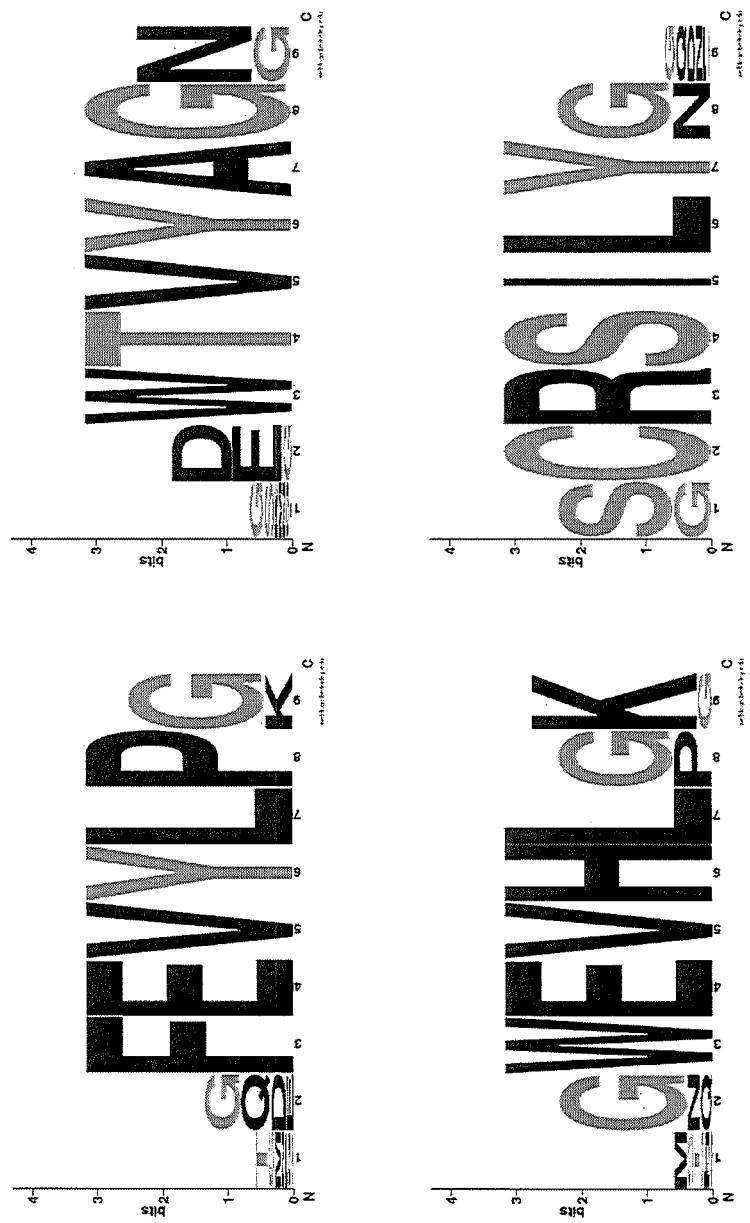
FIG. 12 is a LOGO plot of consensus motifs (SEQ ID NOS 83-84, 3 and 85, respectively, in order of appearance) for the prostate specific antigen (PSA) binders generated through the three-step approach (Example 4).

Four sequences, FEVYL (SEQ ID NO: 1), WTVYA (SEQ ID NO: 2), WEVHL (SEQ ID NO: 3), and RSILY (SEQ ID NO: 4), selected from the 5-mer Array were extended by all possible dimers at both N- and C-terminus using all 20 natural amino acids (X) to design Extension Arrays each of them consisting of 160,000 members synthesized in 5 replicates (Table 2). Top twelve sequences for each library selected by signal intensity of PSA binding were used to generate Logo plots shown in FIG. 12. FIG. 12 demonstrates that the core 5-mer sequences prefer specific amino acids at the flanking regions in order to obtain the highest PSA binding signal. For example, FEVYL motif (SEQ ID NO: 1) prefers exclusively P at the C-terminus, WTVYA motif (SEQ ID NO: 2) prefers acidic amino acid either D or E at the N-terminus and G at the C-terminus, whereas RSILY motif (SEQ ID NO: 4) prefers C at the C-terminus, an amino acid that was not present in the 5-mer arrays.

TABLE 2

| Sequences selected from 5-mer libraries | SEQ ID NO: | Extension libraries | Sequences selected from extension libraries | SEQ ID NO: |
|---|---|---|---|---|
| FEVYL | 1 | XXFEVYLXX | NGFEVYLPG | 5 |
| WTVYA | 2 | XXWTVYAXX | SEWTVYAGN | 6 |
| WEVHL | 3 | XXWEVHLXX | TGWEVHLGK | 7 |
| RSILY | 4 | XXRSILYXX | SCRSILYGQ | 8 |
| Double substitution/ deletion libraries | SEQ ID NO: | substitution/ deletion libraries | Sequences selected from SEQ | SEQ ID NO: |
| GNGFEVYLPGG | 42 | GTGFEVYIPGA | | 9 |
| GSEWTVYAGNG | 43 | ASEWTVYAGNK | | 10 |
| GTGWEVHLGKG | 11 | GTGWEVHLGKG | | 11 |
| GSCRSILYGQG | 44 | QSCRSILYGDG | | 12 |

The top sequences selected from the Extension Array (Table 2, column 3) were used to design Double Substitution/Deletion Arrays as shown in column 4 of Table 2. Single and double substitution scan performed as described in Example 3 were used to optimize PSA binders to achieve highest signal intensity and confirm specificity of each amino acid in motif sequence (Table 2, column 5).

While the invention has been described in detail with reference to specific examples, it will be apparent to one skilled in the art that various modifications can be made within the scope of this invention. Thus the scope of the invention should not be limited by the examples described herein, but by the claims presented below.

We claim:

1. A method of identifying a peptide binder comprising the steps of:
   (a) exposing a protein target of interest to a first peptide microarray produced by maskless photolithography comprising a first population of peptide binders, whereby the protein target binds to peptide binders of the first population of peptide binders;
   (b) identifying overlap in sequences of the peptide binders of the first population of peptide binders which bind the protein target of interest, whereby a core binder sequence of the first population of peptide binders is determined;
   (c) performing at least one alteration to each core binder sequence of the first population of peptide binders wherein the alteration is selected from a single amino acid substitution, a double amino acid substitution, an amino acid insertion, and an amino acid deletion, whereby a second population of peptide core binder sequences is generated; and
   (d) exposing the protein target of interest to a second peptide microarray produced by maskless photolithography comprising the second population of peptide core binder sequences generated in step (c), whereby the protein target binds to at least one of the altered peptide core binder sequences of the second population of peptide core binder sequences; and
   (e) identifying one or more sequences of the second population of peptide core binder sequences demonstrating strong binding properties to the protein target, whereby a mature core binding sequence is determined;
   wherein:
   the first peptide microarray comprises at least $1.0 \times 10^6$ peptides; and
   the first population of peptide binders comprise all 5-mer peptides comprising all 20 natural amino acid excluding cysteine and optionally excluding methionine and the 5-mer peptides have the amino acid sequence -$M_1M_2M_3M_4M_5$-.

2. The method of claim 1, wherein the alteration in step (c) comprises the single amino acid substitution or the double amino acid substitution and the single amino acid substitution or the double amino acid substitution occurs at each of $M_1$, $M_2$, $M_3$, $M_4$, and $M_5$ using each of the other 18 natural amino acids.

3. The method of claim 1, wherein the alteration in step (c) comprises the amino acid insertion and the amino acid insertion occurs before or after one of $M_1$, $M_2$, $M_3$, $M_4$, and $M_5$.

4. The method of claim 1, wherein the alteration in step (c) comprises the amino acid deletion and the amino acid deletion occurs at one of $M_1$, $M_2$, $M_3$, $M_4$, and $M_5$ to form 4-mer peptides.

5. The method of claim 4, wherein the 4-mer peptides are further altered and the alteration is selected from a single amino acid substitution, a double amino acid substitution, an amino acid insertion.

6. The method of claim 1, wherein the alteration in step (c) to each core binder sequence of the first population of peptide binders comprises the single amino acid substitution and the single amino acid substitution occurs at one of $M_1$, $M_2$, $M_3$, $M_4$, and $M_5$ using each of the other 18 natural amino acids; the single amino acid insertion and the single amino acid insertion occurs before or after one of $M_1$, $M_2$, $M_3$, $M_4$, and $M_5$; and/or the single amino acid deletion and the single amino acid deletion occurs at one of $M_1$, $M_2$, $M_3$, $M_4$, and $M_5$ to form 4-mer peptides.

7. The method of claim 6, wherein the 4-mer peptides are further altered and the alteration is selected from a single amino acid substitution, a double amino acid substitution, an amino acid insertion.

8. The method of claim 1, wherein the second peptide microarray comprises at least $1.0 \times 10^6$ peptides.

9. The method of claim 6, wherein the second peptide microarray comprises at least $1.2 \times 10^6$ peptides.

10. The method of claim 9, wherein the second peptide microarray comprises at least $1.8 \times 10^6$ peptides.

11. The method of claim 1, wherein the first peptide microarray comprises at least $1.2 \times 10^6$ peptides.

12. The method of claim 11, wherein the first peptide microarray comprises at least $1.8 \times 10^6$ peptides.

13. The method of claim 1, wherein the second population of peptide binders comprise natural amino acids, non-natural amino acids, or combinations thereof.

14. The method of claim 1, wherein the second population of peptide binders comprise linear peptides, cyclic peptides, constrained peptides, or combinations thereof.

15. The method of claim 1 further comprising:
(f) performing at least one of N-terminal and C-terminal extension of the mature core binding sequence determined in step (e), whereby a third population of peptide extended mature core binder sequences is generated; and
(g) exposing the protein target of interest to a third peptide microarray produced by maskless photolithography comprising the third population of peptide extended mature core binder sequences generated in step (f), whereby the protein target binds to at least one of the extended peptide mature core binder sequences of the third population of peptide extended mature core binder sequences; and
(h) identifying overlap in the N-terminal or C-terminal peptide binder sequences of the peptides comprising the population of extended mature core binders, whereby an extended, matured core binder sequence is determined.

16. The method of claim 15, wherein the third peptide microarray comprises at least $1.0 \times 10^6$ peptides.

* * * * *

UNITED STATES PATENT AND TRADEMARK OFFICE
CERTIFICATE OF CORRECTION

| | |
|---|---|
| PATENT NO. | : 10,976,317 B2 |
| APPLICATION NO. | : 16/191407 |
| DATED | : April 13, 2021 |
| INVENTOR(S) | : Patel et al. |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 56 days.

Signed and Sealed this
Thirty-first Day of January, 2023

Katherine Kelly Vidal
*Director of the United States Patent and Trademark Office*